US011052128B2

(12) United States Patent
Olbrich et al.

(10) Patent No.: US 11,052,128 B2
(45) Date of Patent: Jul. 6, 2021

(54) FORMULATION FOR BISPECIFIC T-CELL ENGAGERS (BITES)

(71) Applicant: AMGEN INC., Thousand Oaks, CA (US)

(72) Inventors: Carsten Olbrich, Berlin (DE); Thomas Bunte, Berlin (DE); Jonas Winter, Berlin (DE); Jörg Peters, Berlin (DE); Thomas Trill, Berlin (DE)

(73) Assignee: AMGEN INC., Thousand Oaks, CA (US)

( * ) Notice: Subject to any disclaimer, the term of this patent is extended or adjusted under 35 U.S.C. 154(b) by 237 days.

(21) Appl. No.: 14/441,069

(22) PCT Filed: Nov. 5, 2013

(86) PCT No.: PCT/EP2013/073024
§ 371 (c)(1),
(2) Date: May 6, 2015

(87) PCT Pub. No.: WO2014/072277
PCT Pub. Date: May 15, 2014

(65) Prior Publication Data
US 2015/0335706 A1      Nov. 26, 2015

(30) Foreign Application Priority Data
Nov. 6, 2012 (EP) ..................................... 12191493

(51) Int. Cl.
| C07K 16/00 | (2006.01) |
| A61K 38/17 | (2006.01) |
| C07K 16/30 | (2006.01) |
| C07K 16/28 | (2006.01) |
| A61K 39/395 | (2006.01) |

(52) U.S. Cl.
CPC ........ *A61K 38/17* (2013.01); *A61K 39/39591* (2013.01); *C07K 16/2809* (2013.01); *C07K 16/3069* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| 6,171,586 B1 * | 1/2001 | Lam ................. A61K 39/39591 424/130.1 |
| 8,481,692 B2 * | 7/2013 | Sidhu ..................... A61P 37/02 530/409 |
| 9,260,522 B2 * | 2/2016 | Kufer ................. C07K 16/2809 |

FOREIGN PATENT DOCUMENTS

| WO | WO 2007/034198 | 3/2007 |
| WO | WO 2008/081166 | 7/2008 |
| WO | WO 2008/084237 | 7/2008 |
| WO | WO 2008/119566 | 10/2008 |
| WO | WO 2008/119567 | 10/2008 |
| WO | WO 2009/070642 | 6/2009 |
| WO | WO/2010/037836 | * 4/2010 |
| WO | WO 2010/037836 | 4/2010 |
| WO | WO 2010/148337 | 12/2010 |
| WO | WO 2011/061712 | 5/2011 |

OTHER PUBLICATIONS

Baeuerle et al., "BiTE: Teaching antibodies to engage in T-cells for cancer therapy", *Current Opinion in Molecular Therapeutics*, vol. 11, No. 1, (2009), pp. 22-30.
Choi et al., "Bispecific antibodies engage T cells for antitumor immunotherapy", *Expert Opin. Biol. Ther.*, vol. 11, No. 7, (2011), pp. 843-853.

* cited by examiner

*Primary Examiner* — Meera Natarajan
(74) *Attorney, Agent, or Firm* — Marshall, Gerstein & Borun LLP

(57) ABSTRACT

The present invention relates to stable pharmaceutical compositions which contain polypeptides having at least two antigen-binding domains and are especially suited for subcutaneous administration. The invention provides liquid compositions which minimize the formation of undesired polypeptide aggregates (dimers and/or multimers). The present invention further provides a method for minimizing the aggregation of polypeptides having antigen-binding domains in liquid compositions.

9 Claims, No Drawings

Specification includes a Sequence Listing.

SEQUENCE LISTING

<160> NUMBER OF SEQ ID NOS: 8

<210> SEQ ID NO 1
<211> LENGTH: 27
<212> TYPE: PRT

```
<213> ORGANISM: Homo sapiens

<400> SEQUENCE: 1

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25

<210> SEQ ID NO 2
<211> LENGTH: 27
<212> TYPE: PRT
<213> ORGANISM: Callithrix jacchus

<400> SEQUENCE: 2

Gln Asp Gly Asn Glu Glu Met Gly Asp Thr Thr Gln Asn Pro Tyr Lys
1               5                   10                  15

Val Ser Ile Ser Gly Thr Thr Val Thr Leu Thr
            20                  25

<210> SEQ ID NO 3
<211> LENGTH: 27
<212> TYPE: PRT
<213> ORGANISM: Saguinus oedipus

<400> SEQUENCE: 3

Gln Asp Gly Asn Glu Glu Met Gly Asp Thr Thr Gln Asn Pro Tyr Lys
1               5                   10                  15

Val Ser Ile Ser Gly Thr Thr Val Thr Leu Thr
            20                  25

<210> SEQ ID NO 4
<211> LENGTH: 27
<212> TYPE: PRT
<213> ORGANISM: Saimiri sciureus

<400> SEQUENCE: 4

Gln Asp Gly Asn Glu Glu Ile Gly Asp Thr Thr Gln Asn Pro Tyr Lys
1               5                   10                  15

Val Ser Ile Ser Gly Thr Thr Val Thr Leu Thr
            20                  25

<210> SEQ ID NO 5
<211> LENGTH: 249
<212> TYPE: PRT
<213> ORGANISM: Artificial Sequence
<220> FEATURE:
<223> OTHER INFORMATION: scFv binding domain CD3

<400> SEQUENCE: 5

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95
```

```
Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 6
<211> LENGTH: 243
<212> TYPE: PRT
<213> ORGANISM: Artificial Sequence
<220> FEATURE:
<223> OTHER INFORMATION: scFv binding domain PSMA

<400> SEQUENCE: 6

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
            130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Arg Tyr Ser
            180                 185                 190

Asp Val Pro Ser Arg Phe Ser Gly Ser Ala Ser Gly Thr Asp Phe Thr
        195                 200                 205
```

```
Leu Thr Ile Ser Ser Val Gln Ser Glu Asp Phe Ala Thr Tyr Tyr Cys
            210                 215                 220

Gln Gln Tyr Asp Ser Tyr Pro Tyr Thr Phe Gly Gly Gly Thr Lys Leu
225                 230                 235                 240

Glu Ile Lys

<210> SEQ ID NO 7
<211> LENGTH: 498
<212> TYPE: PRT
<213> ORGANISM: Artificial Sequence
<220> FEATURE:
<223> OTHER INFORMATION: PSMA-BiTE

<400> SEQUENCE: 7

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
            85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
            165                 170                 175

Gly Gln Ala Pro Lys Ser Leu Ile Tyr Ser Ala Ser Tyr Arg Tyr Ser
        180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
            210                 215                 220

Gln Gln Tyr Asp Ser Tyr Pro Tyr Thr Phe Gly Gly Gly Thr Lys Leu
225                 230                 235                 240

Glu Ile Lys Ser Gly Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320
```

```
Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Gly Gly Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu

<210> SEQ ID NO 8
<211> LENGTH: 504
<212> TYPE: PRT
<213> ORGANISM: Artificial Sequence
<220> FEATURE:
<223> OTHER INFORMATION: Sequence of PSMA-BiTE1

<400> SEQUENCE: 8

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
            85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
            165                 170                 175

Gly Gln Ala Pro Lys Ser Leu Ile Tyr Ser Ala Ser Tyr Arg Tyr Ser
```

-continued

```
                180             185             190
Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
        210                 215                 220

Gln Gln Tyr Asp Ser Tyr Pro Tyr Thr Phe Gly Gly Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu His His His His His His
                500
```

FORMULATION FOR BISPECIFIC T-CELL ENGAGERS (BITES)

INTRODUCTION

The present invention relates to stable pharmaceutical compositions which contain polypeptides having at least two antigen-binding domains and are especially suited for subcutaneous administration. The invention provides liquid compositions which minimize the formation of undesired polypeptide aggregates (dimers and/or multimers). The present invention further provides a method for minimizing the aggregation of polypeptides having antigen-binding domains in liquid compositions.

PRIOR ART

The need to stabilize antibodies in solution, i.e. to prevent the formation of dimers and multimers (known as High Molecular Weight or HMW aggregates), in order to keep the therapeutic efficacy constant is known in the prior art. WO2011061712 discloses stabilized antibody formulations which, in addition to 25-250 mg/ml antibody, contain 10-30 mM of a buffer (preferably acetate, succinate, phosphate, histidine or combinations thereof), 1-15% of a polyol and also 0.001-0.05% of a wetting agent. The pH of the compositions is between 5-7.5.

WO2010148337(A1) ("Lyophilized formulation for small modular immunopharmaceuticals") discloses compositions of what are known as Small Immunopharmaceutical Proteins (SMIP). These are constructs composed of multiple fused domains, for example an antigen-binding domain, an immunoglobulin hinge region and a $C_H2$ or $C_H3$ region of an Ig molecule or a region derived therefrom. The domains of the SMIPs consist of polypeptides which are products of gene sequences which may be of human, non-human or artificial (generated using gene-technology methods) origin. Although SMIP proteins are preferably monospecific, the application also discloses multispecific variants, for example Scorpion molecules. They contain SMIP proteins having a further C-terminal binding domain. The binding domains of the Scorpion molecules bind preferably to different target structures and are therefore suitable as immunospecific therapeutics. WO2010148337(A1) discloses stable formulations of lyophilized compositions containing an SMIP, with less than 7% of the SMIP being present in aggregated form. Said formulations can further comprise buffer agents, stabilizers, bulking agents, wetting agents and further excipients. WO2009070642 A1 discloses various formulations of the BiTE molecule MT103, the first binding domain of which binds specifically to the T-cell receptor antigen CD3, whereas the second binds specifically to the B-cell antigen CD19. The BiTE molecules are stable in the disclosed compositions up to a maximum concentration of 300 µg/ml, at a pH of 7.0. The buffer used is citrate. The formulations are suited for intravenous and subcutaneous administration. The bioavailability after subcutaneous administration is 10-50%.

IgG antibodies have large constant regions ($C_{H1-3}/C_L$ regions), which are responsible for the majority of their physicochemical properties. IgG antibodies having varying specificity differ structurally mainly in the region of the hypervariable antibody binding sites (CDR1-CDR3) within the $V_L$ and $V_H$ regions. The structural and physicochemical differences between the individual IgG variants are relatively small owing to the large constant regions. Like IgG antibodies, the SMIP molecules described in WO2010148337 (A1) contain parts of the constant antibody domain.

By contrast, BiTE molecules having varying specificity differ markedly in their physicochemical properties. As fusion protein composed of two single-chain variable fragments (scFv) of, in general, different immunoglobulins, they lack the constant $C_{H1-3}/C_L$ regions, and so differences in the antigen-binding domains concern much larger sections of the BiTE molecules than is the case for IgG or SMIP antibodies. Likewise, the BiTE molecule MT103 and the BiTE molecules which are used in the present invention differ principally in their molecular structure. Whereas the domains in MT103 are arranged in the sequence $V_L$-$V_H$-$V_H$-$V_L$, the arrangement for BiTE molecules which are preferably used in the present invention is of the form $V_H$-$V_L$-$V_H$-$V_L$. Furthermore, the sequences of both molecules differ at numerous positions.

These properties of the BiTE molecules and their small size give rise to distinct differences in the physicochemical behaviour of different BiTE molecules. This results in the need to develop individual formulations (to increase the physicochemical stabilities) for each individual application, since the formulations of individual BiTEs or similar molecules cannot be used, or can only be used with restrictions, for alternative applications.

In one embodiment, the polypeptides present in the compositions are what are known as Bispecific T-cell engagers (BiTEs). In a specific embodiment, BiTEs have a first binding domain which binds specifically to the E chain of the T-cell receptor-CD3 complex and a second binding domain which binds specifically to prostate-specific membrane antigen (PSMA). PSMA is an integral type II membrane protein which is expressed on prostate epithelial cells with high specificity and, in the event of prostate cancer, at increased intensity. Furthermore, PSMA is expressed by newly formed blood vessels of solid tumours. PSMA-BiTEs thus mediate direct contact between cytotoxic T cells and these target cells.

Aggregate formation in proteins, for example BiTE molecules, is undesirable in pharmaceutical applications, for example the efficacy or availability of a biological active ingredient can be altered by aggregate formation.

This results in the object of providing a formulation which allows BiTE molecules to be stabilized in such a way that undesired aggregate formation is suppressed.

The solution is set forth in the present application and in the claims and encompasses a BiTE formulation comprising TRIS and phosphate. In its preferred embodiment, the formulation comprises 50 mM phosphate, 100 mM TRIS, 0.04% polysorbate 80 and 4% trehalose dihydrate at a pH of 6.0 and is capable of stabilizing formulations with PSMA-BiTE1 molecules with respect to the formation of aggregates. This applies both to low concentrations in the range of below µg/ml and to high concentrations of >2 mg/ml. The stabilizing effect is surprising for a person skilled in the art, since, for example, the citrate used in WO2009070642 A1, even as a combination of 50 mM citrate and 100 mM TRIS at pH 6.0, does not exhibit this effect. For instance, the measured dimer fraction in a comparable composition which contained only citrate instead of phosphate was 7.0%. By contrast, the composition according to the invention limited the dimer fraction to 0.8% (cf. tables 6 and 7). The combined use of TRIS and phosphate is responsible for the stabilizing effect of the compositions. To stabilize the BiTE molecules with respect to shear forces as well, a wetting agent such as polysorbate 80 in a concentration of at least 0.04% is required, since the dimer fraction will otherwise be too large (approx. 7.5%, see table 15). To prevent the adsorption of the PSMA-BiTE1 molecules on the vessel wall of injection syringes, infusion bags, etc., it is sufficient to have just 0.002% polysorbate 80.

DEFINITIONS

The term "antibody" used herein refers to immunoglobulin molecules which each comprise two heavy (H) and two light (L) polypeptide chains which are connected to one another via disulphide bonds. Each heavy chain consists of a variable region ($V_H$) and a constant region, which in turn consists of three domains ($C_H1$, $C_H2$ and $C_H3$). Each of the light chains is composed of a variable region ($V_L$) and a constant region ($C_L$). The variable regions of both the light and the heavy chains ($V_H$ and $V_L$) are further subdivided into, in each case, three hypervariable antibody binding sites (CDR1-CDR3) and altogether four conserved regions between the CDRs (FR1-FR4).

The term "monoclonal antibody" describes an antibody which originates from a population of antibodies which are identical with the exception of relatively small, naturally occurring mutations or post-translational modifications. In contrast to polyclonal antibodies, as appear as part of the immune response, monoclonal antibodies are directed against a specific epitope.

A "bispecific" or "bifunctional antibody" is an artificial, hybrid antibody having two different pairs of heavy and light chain and also two different antigen-binding sites.

Treatment of antibodies with papain leads to two identical, antigen-binding Fab fragments and to the crystallizable Fc fragment. A "Fab fragment" consists of a complete $V_L$ chain and part of the heavy chain, viz. the $V_H$ domain containing the variable region and the first constant domain $C_H1$. Each Fab fragment thus has an individual antigen-binding site. The "Fc fragment" comprises the carboxy-terminal parts of both heavy chains, linked via disulphide bonds. Parts of the Fc fragment are recognized by Fc receptors of other cells and determine via this the effector functions of the antibodies.

Pepsin cleaves antibodies below the disulphide bonds, and so the two Fab fragments remain connected via the hinge region and a single "F(ab')2 fragment" is formed. It has both antigen-binding sites and is therefore capable, like the complete antibody, of cross-linking antigens.

The term "domain" describes a globular region of a protein having a defined and independently folded structure. The light chains of an IgG antibody are composed of two domains (in each case, a constant and a variable domain); the heavy chains are composed of four domains (in each case, three constant and one variable domain). The two variable regions are each composed of one domain of the heavy chain and one domain of the light chain.

The term "epitope" or "antigenic determinant" describes the area of an antigen to which an antibody (or the antigen-binding fragment thereof) specifically binds. Epitopes can consist of successive amino acids, or of non-successive amino acids which are in close proximity to one another as a result of tertiary protein folding.

An "antigen" is a molecule (e.g. a protein, polypeptide, peptide, carbohydrate) having an "antigenic determinant" to which an antibody can bind.

The term "conformation" refers to the tertiary structure of a protein or polypeptide, for example an antibody, an antibody chain, a domain or a part thereof.

An antibody which "specifically binds" a particular polypeptide or an epitope on a particular polypeptide, or is "specific for" this structure, binds to alternative structures considerably less effectively.

The term "scFv antibody" in this application refers to artificially produced antibody fragments consisting of covalently bonded $V_H$ and $V_L$ domains of an antibody. Both domains are present in a single polypeptide chain and are connected to one another via a polypeptide linker composed of multiple amino acids. With the exception of the Fc-mediated effector functions, scFv antibodies retain all functions of an antibody, more particularly its selectivity and affinity.

"Bispecific T-cell engager" (BiTE) molecules are recombinant protein constructs composed of two flexibly connected single-chain antibodies (scFv). One of said scFv antibodies binds specifically to a selected, target cell-expressed tumour antigen, the second binds specifically to CD3, a subunit of the T-cell receptor complex on T cells. The BiTE antibodies are capable of binding T cells transiently to target cells and, at the same time, activating the cytolytic activity of the T cells. The BiTE-mediated activation of the T cells requires neither specific T-cell receptors on the T cells, nor MHC I molecules, peptide antigens or co-stimulatory molecules on the target cell.

The terms "stability" and "stable" in the context of BiTE molecule-containing compounds describe the resistance of the antibodies or their fragments with respect to aggregation, degradation or fragmentation under the given conditions relating to their production, preparation, storage, use or transport. "Stable" formulations according to the present invention retain their biological activity under the given production, preparation, transport, use and storage conditions.

Proteins present in solution (e.g. BiTE molecules) are sensitive to mechanical movement, as occurs during production, container-filling and transport. Above a certain intensity of movement, the molecules aggregate and/or denature. Liquid, protein-containing compositions are thus exposed to what is known as agitation stress during mechanical movement. In an "agitation stress test", the controlled use of mechanical (agitation) forces on liquid, protein-containing compositions is used to analyse the aggregation and denaturation behaviour of the dissolved protein in different compositions.

The behaviour of a protein in the agitation stress test is an indication of its physical stability with respect to shear forces, as occur, for example, during aspiration and injection of solutions with cannulae.

"Lyophilization" describes a drying method which is based on the principle of sublimation. The substance to be dried is firstly cooled down to about −45° C. before a vacuum is subsequently applied and the substance is heated to about −20° C. As a result, the ice crystals sublime directly into the gaseous state without passage through a liquid intermediate step. The substance dried in this manner contains, after a secondary drying step (still under vacuum) at about 25° C., less than 5% of its original moisture and is referred to as a "lyophilisate".

Prior to administration to the patient, the lyophilisate is "reconstituted", i.e. dissolved in a pharmaceutically acceptable diluent. A "reconstituted formulation" in the context of the present invention is formed by dissolving a lyophilized antibody formulation in such a diluent. The antibody is subsequently in dissolved form and can be administered to the patient.

"Polyols" describe a group of organic compounds which contain multiple hydroxyl groups (—OH) (polyalcohol, polyhydric alcohol). Polyols such as sucrose or trehalose are sugars which are capable of stabilizing antibodies and/or influencing the osmolarity of a composition.

To prevent undesired degradation or aggregation of proteins during lyophilization, so-called "lyoprotectants" are added. These are, for example, sugars or sugar alcohols such as sucrose, mannose, trehalose, glucose, sorbitol, mannitol. In the context of the present invention, trehalose is the lyoprotectant which is preferably used.

The term "wetting agent" herein refers to any detergent having a hydrophilic and a hydrophobic region and includes non-ionic, cationic, anionic and zwitterionic detergents. Usable detergents encompass, for example, polyoxyethylene sorbitan monooleate (also known as polysorbate 80 or TWEEN 80), polyoxyethylene sorbitan monolaurate (also known as polysorbate 20 or TWEEN 20), or N-laurylsarcosine. For the compositions disclosed herein, preference is given to a non-ionic wetting agent. Particular preference is given to the use of polysorbate 80 for the compositions of the present invention. The wetting agent can be used in a concentration of from 0.002% to 0.1%.

The term "buffer" describes herein a buffered solution, the pH of which changes only slightly after addition of acidic or alkaline substances. Buffered solutions contain a mixture of a weak acid and its corresponding base or of a weak base and its corresponding acid.

The term "patient" refers to (human or animal) individuals receiving a preventive or therapeutic treatment.

The term "treatment" herein refers to the use or administration of a therapeutic substance on/to a patient, or to the use or administration of a therapeutic substance on/to an isolated tissue or on/to a cell line of a patient, who is suffering from a disease, is showing a symptom of a disease, or has a predisposition to a disease, with the goal of curing, improving, influencing, stopping or alleviating the disease, its symptoms or the predisposition to the disease.

"Effective dose" describes herein the active-ingredient amount with which the desired effect can be at least partially achieved. A "therapeutically effective dose" is therefore defined as the active-ingredient amount which is sufficient to at least partially cure a disease, or to at least partially eliminate adverse effects in the patient that are caused by the disease. The amounts actually required for this purpose are dependent on the severity of the disease and on the general immune status of the patient.

The term "bioavailability", as used here, describes the percentage of an active ingredient or of a medicinal-product dose which is available unaltered in the systemic circulation. Bioavailability is thus a measured value indicating how rapidly and to what extent the active ingredient is absorbed and available at the site of action. By definition, intravenously administered medicinal products have a bioavailability of 100%.

Absolute bioavailability describes the bioavailability of a substance administered in any desired (non-intravenous) manner compared to intravenous administration, whereas relative bioavailability results from a comparison of the bioavailabilities for particular dosage forms (e.g. oral vs. subcutaneous).

An "isotonic compound" has substantially the same osmotic pressure as human blood. Isotonic compounds therefore have in general an osmotic pressure of about 250 to 350 mOsm. The term "hypotonic" describes compositions having an osmotic pressure below that of human blood, whereas "hypertonic" compositions have an osmotic pressure above that of human blood.

The term "high-molecular-weight aggregates" (synonym: "HMW") describes aggregates which are composed of at least two protein monomers.

The term "phosphates" used herein refers to water-soluble, pharmacologically safe salts of the tribasic orthophosphoric acid ($H_3PO_4$), with preference being given to primary (hydrogen-) and secondary (dihydrogen-) phosphates. The compositions according to the invention contain preferably sodium phosphates, particularly preferably disodium hydrogenphosphate ($Na_2HPO_4$).

DETAILED DESCRIPTION

The invention relates to the pharmaceutical formulation of a bispecific T-cell engager (BiTE) molecule, characterized in that it comprises tris(hydroxymethyl)aminomethane (TRIS) and phosphate.

BiTE molecules are known in the prior art. BiTE molecules are designed in such a way that they transiently enlist cytotoxic T cells for the lysis of particular target cells (see Bäuerle et al. Curr Opin Mol Ther. 2009 February; 11(1): 22-30.). They are especially suitable for cancer therapy.

A BiTE molecule is a polypeptide which comprises two scFv antibody binding domains, with the first scFv binding domain being able to bind to human CD3 epsilon and the second scFv binding domain binding a second, further surface antigen. Preference is given to human surface antigens of cancer cells. Particularly preferred surface antigens are human surface proteins of cancer cells. The scFv binding domains can comprise chimeric, humanized or human antibody fragments. Preferably, the scFv binding domains comprise human or humanized antibody fragments.

The BiTE molecules used in the present invention differ from the BiTE molecules (e.g. MT103) as described, for example, in WO2009070642 A1 in that the first binding domain can bind to an epitope of the human and Callithrix jacchus, Saguinus oedipus or Saimiri sciureus CD3 epsilon chain, with the epitope being part of an amino acid sequence selected from the group consisting of SEQ ID NO: 1, 2, 3 and 4 and the epitope comprising at least the amino acid sequence Gln-Asp-Gly-Asn-Glu. This has the advantage that preclinical investigations are facilitated, since, for example, pharmacokinetic or toxicological studies can be carried out in the aforementioned test animals, whose immune system is similar to that of humans. BiTE molecules having these characteristics are disclosed, for example, in WO2008119566 A2 or WO2008119567 A2.

In one embodiment, the composition according to the invention thus comprises BiTE molecules, the first binding domain of which can bind to an epitope of the human and Callithrix jacchus, Saguinus oedipus or Saimiri sciureus CD3 epsilon chain, with the epitope being part of an amino acid sequence selected from the group consisting of SEQ ID NO: 1, 2, 3 and 4 and the epitope comprising at least the amino acid sequence Gln-Asp-Gly-Asn-Glu.

SEQ ID NO: 5 displays the amino acid sequence of an scFV binding domain which meets the above criteria.

In a preferred embodiment, the first binding domain of the polypeptide comprises the amino acid sequence reproduced in SEQ ID NO: 5.

scFV comprises the amino acids of a variable light (VL) and a variable heavy (VH) antibody chain. BITE molecules can be constructed in varying orientation. The BiTE molecule MT103 has, for example, a (VL-VH) binding domain 2-(VH-VL) binding domain 1 arrangement of the scFVs.

Other orientations are also possible, for example (VH-VL) binding domain 2-(VH-VL) binding domain 1.

In a preferred embodiment, the polypeptide has the arrangement (VH-VL) binding domain 2-(VH-VL) binding domain 1.

In a particularly preferred embodiment, the polypeptide has the arrangement (VH-VL) binding domain 2-(VH-VL) binding domain 1, with (VH-VL) binding domain 1 comprising the amino acid sequence reproduced in SEQ ID NO: 5.

One embodiment of the present invention is a liquid pharmaceutical composition, characterized in that the second binding domain can bind to a cell surface antigen. A cell surface antigen is an antigen which can be bound by a binding protein, for example an antibody or an scFv, without the cell having to be lysed.

One embodiment of the present invention is a liquid pharmaceutical composition, characterized in that the second binding domain of the polypeptide can bind to a surface antigen of a cancer cell.

In a further embodiment, the second binding domain of the polypeptide binds to the human surface antigen prostate-specific membrane antigen (PSMA, SWISS-PROT: FOLH1_HUMAN, accession no: Q04609). Such BiTE molecules are described, for example, in WO2010037836 A2.

SEQ ID NO: 6 describes a binding domain which binds to PSMA.

In a preferred embodiment, the second binding domain of the polypeptide comprises the amino acid sequence reproduced in SEQ ID NO: 6.

One embodiment of the present invention is a liquid pharmaceutical composition comprising a polypeptide which comprises a first and a second scFv binding domain, with the first binding domain comprising the amino acid sequence reproduced in SEQ ID NO: 5, characterized in that the composition further comprises TRIS and phosphate.

One embodiment of the present invention is a liquid pharmaceutical composition, characterized in that the binding domains of the polypeptide comprise human or humanized scFv antibody fragments.

One embodiment of the present invention is a liquid pharmaceutical composition, characterized in that the second PSMA-binding binding domain comprises the amino acid sequence reproduced in SEQ ID NO: 6.

In one embodiment, the polypeptide comprises the amino acid sequences of the first and second binding domain encoded by the sequences reproduced in SEQ ID NO: 5 and SEQ ID NO: 6.

A polypeptide which comprises the sequences reproduced in SEQ ID NO: 5 and SEQ ID NO: 6 is reproduced in SEQ ID NO: 7 or SEQ ID NO: 8.

A preferred polypeptide comprises the amino acid sequence reproduced in SEQ ID NO: 7.

A particularly preferred polypeptide is the PSMA-BiTE 1 molecule, which is encoded by the amino acid sequence reproduced in SEQ ID NO: 8.

A preferred embodiment of the present invention is a liquid pharmaceutical composition comprising a polypeptide, TRIS and phosphate, with the polypeptide comprising the amino acid sequence reproduced in SEQ ID NO: 7.

A particularly preferred embodiment of the present invention is a liquid pharmaceutical composition comprising a polypeptide, TRIS and phosphate, with the polypeptide comprising the amino acid sequence reproduced in SEQ ID NO: 8.

In one embodiment, the composition according to the invention comprises about 0.5 µg/ml, about 0.7 µg/ml, about 1 µg/ml, about 2 µg/ml, about 5 µg/ml, about 6 µg/ml, about 10 µg/ml, about 15 µg/ml, about 18 µg/ml, about 20 µg/ml, about 25 µg/ml, about 30 µg/ml, about 30 µg/ml, about 35 µg/ml, about 40 µg/ml, about 45 µg/ml, about 50 µg/ml, about 55 µg/ml, about 60 µg/ml, about 70 µg/ml, about 80 µg/ml, about 90 µg/ml, about 100 µg/ml, about 110 µg/ml, about 120 µg/ml, about 130 µg/ml, about 140 µg/ml, about 150 µg/ml, about 160 µg/ml, about 170 µg/ml, about 180 µg/ml, about 190 µg/ml, about 200 µg/ml, about 225 µg/ml, about 275 µg/ml, about 300 µg/ml, about 325 µg/ml, about 350 µg/ml, about 375 µg/ml, about 400 µg/ml, about 500 µg/ml, about 700 µg/ml, about 900 µg/ml, or about 1000 µg/ml of the above-mentioned polypeptides.

In one embodiment, the composition according to the invention comprises 0.5 µg/ml, 0.7 µg/ml, 1 µg/ml, 2 µg/ml, 5 µg/ml, 6 µg/ml, 10 µg/ml, 15 µg/ml, 18 µg/ml, 20 µg/ml, 25 µg/ml, 30 µg/ml, 30 µg/ml, 35 µg/ml, 40 µg/ml, 45 µg/ml, 50 µg/ml, 55 µg/ml, 60 µg/ml, 70 µg/ml, 80 µg/ml, 90 µg/ml, 100 µg/ml, 110 µg/ml, 120 µg/ml, 130 µg/ml, 140 µg/ml, 150 µg/ml, 160 µg/ml, 170 µg/ml, 180 µg/ml, 190 µg/ml, 200 µg/ml, 225 µg/ml, 275 µg/ml, 300 µg/ml, 325 µg/ml, 350 µg/ml, 375 µg/ml, 400 µg/ml, 500 µg/ml, 700 µg/ml, 900 µg/ml, or 1000 µg/ml of the BiTE molecules.

In a further embodiment, the composition according to the invention comprises about 1 mg/ml, about 1.3 mg/ml, about 1.5 mg/ml, about 1.8 mg/ml, about 2 mg/ml, about 2.3 mg/ml, about 2.5 mg/ml, about 2.8 mg/ml, about 3 mg/ml, about 3.5 mg/ml, about 4 mg/ml, about 5 mg/ml, about 6 mg/ml, about 7 mg/ml, about 8 mg/ml, about 9 mg/ml or about 10 mg/ml of the BiTE molecules.

In a further embodiment, the composition according to the invention comprises 1 mg/ml, 1.3 mg/ml, 1.5 mg/ml, 1.8 mg/ml, 2 mg/ml, 2.3 mg/ml, 2.5 mg/ml, 2.8 mg/ml, 3 mg/ml, 3.5 mg/ml, 4 mg/ml, 5 mg/ml, 6 mg/ml, 7 mg/ml, 8 mg/ml, 9 mg/ml or 10 mg/ml of the BiTE molecules.

In a further embodiment, the composition according to the invention comprises from about 0.5 µg/ml to about 1 µg/ml, from about 1 µg/ml to about 5 µg/ml, from about 5 µg/ml to about 10 µg/ml, from about 10 µg/ml to about 20 µg/ml, from about 20 µg/ml to about 50 µg/ml, from about 50 µg/ml to about 90 µg/ml, from about 90 µg/ml to about 120 µg/ml, from about 120 µg/ml to about 150 µg/ml, from about 150 µg/ml to about 180 µg/ml, from about 180 µg/ml to about 200 µg/ml, from about 200 µg/ml to about 250 µg/ml, from about 250 µg/ml to about 280 µg/ml, from about 280 µg/ml to about 300 µg/ml, or from about 300 µg/ml to about 350 µg/ml of the BiTE molecules.

In a further embodiment, the composition according to the invention comprises from 0.5 µg/ml to 1 µg/ml, from 1 µg/ml to 5 µg/ml, from 5 µg/ml to 10 µg/ml, from 10 µg/ml to 20 µg/ml, from 20 µg/ml to 50 µg/ml, from 50 µg/ml to 90 µg/ml, from 90 µg/ml to 120 µg/ml, from 120 µg/ml to 150 µg/ml, from 150 µg/ml to 180 µg/ml, from 180 µg/ml to 200 µg/ml, from 200 µg/ml to 250 µg/ml, from 250 µg/ml to 280 µg/ml, from 280 µg/ml to 300 µg/ml, or from 300 µg/ml to 350 µg/ml of the BiTE molecules.

In a further embodiment, the composition according to the invention comprises from about 350 µg/ml to about 1 mg/ml, from about 350 µg/ml to about 1.3 mg/ml, from about 350 µg/ml to about 1.5 mg/ml, from about 350 µg/ml to about 1.8 mg/ml, from about 350 µg/ml to about 2 mg/ml, from about 350 µg/ml to about 2.3 mg/ml, from about 350 µg/ml to about 2.5 mg/ml, from about 350 µg/ml to about 2.8 mg/ml, from about 350 µg/ml to about 3.0 mg/ml, from about 350 µg/ml to about 3.5 mg/ml, from about 350 µg/ml to about 5 mg/ml, or from about 350 µg/ml to about 10 mg/ml of the BiTE molecules.

In a further embodiment, the composition according to the invention comprises from 350 µg/ml to 1 mg/ml, from 350 µg/ml to 1.3 mg/ml, from 350 µg/ml to 1.5 mg/ml, from 350 µg/ml to 1.8 mg/ml, from 350 µg/ml to 2 mg/ml, from 350 µg/ml to 2.3 mg/ml, from 350 µg/ml to 2.5 mg/ml, from 350 µg/ml to 2.8 mg/ml, from 350 µg/ml to 3.0 mg/ml, from 350 µg/ml to 3.5 mg/ml, from 350 µg/ml to 5 mg/ml, or from 350 µg/ml to 10 mg/ml of the BiTE molecules.

In a further embodiment, the composition according to the invention comprises from 0.5 µg/ml to 10 mg/ml, from 0.5 µg/ml to 5 mg/ml, from 0.5 µg/ml to 3.5 mg/ml, from 0.5 µg/ml to 3.0 mg/ml, from 0.5 µg/ml to 2.8 mg/ml, from 0.5 µg/ml to 2.5 mg/ml, from 0.5 µg/ml to 2.3 mg/ml, from 0.5 µg/ml to 2.0 mg/ml, from 0.5 µg/ml to 1.8 mg/ml, from 0.5 µg/ml to 1.5 mg/ml, from 0.5 µg/ml to 1.3 mg/ml, from 0.5 µg/ml to 1.0 mg/ml, from 0.5 µg/ml to 350 µg/ml, from 0.5 µg/ml to 300 µg/ml, from 0.5 µg/ml to 250 µg/ml of the BiTE molecules.

In a further embodiment, the composition according to the invention comprises from about 0.5 µg/ml to about 10 mg/ml, from about 0.5 µg/ml to about 5 mg/ml, from about 0.5 µg/ml to about 3.5 mg/ml, from about 0.5 µg/ml to about 3.0 mg/ml, from about 0.5 µg/ml to about 2.8 mg/ml, from about 0.5 µg/ml to about 2.5 mg/ml, from about 0.5 µg/ml to about 2.3 mg/ml, from about 0.5 µg/ml to about 2.0 mg/ml, from about 0.5 µg/ml to about 1.8 mg/ml, from about 0.5 µg/ml to about 1.5 mg/ml, from about 0.5 µg/ml to about 1.3 mg/ml, from about 0.5 µg/ml to about 1.0 mg/ml, from about 0.5 µg/ml to about 350 µg/ml, from about 0.5 µg/ml to about 300 µg/ml, from about 0.5 µg/ml to about 250 µg/ml of the BiTE molecules.

In a particularly preferred embodiment, the composition according to the invention comprises about 2 mg/ml of the polypeptides according to the invention.

In a further embodiment, the composition according to the invention comprises a combination of tris(hydroxymethyl) aminomethane (TRIS) and phosphate as buffering, pH-influencing agents.

In a preferred embodiment, the composition according to the invention comprises TRIS in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 150 mM, or of about 200 mM, or of about 250 mM, or of about 300 mM and phosphate in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 150 mM, or of about 200 mM.

In a preferred embodiment, the composition according to the invention comprises TRIS in a concentration of 10 mM, or of 20 mM, or of 30 mM, or of 40 mM, or of 50 mM, or of 60 mM, or of 70 mM, or of 80 mM, or of 90 mM, or of 100 mM, or of 150 mM, or of 200 mM, or of 250 mM, or of 300 mM and phosphate in a concentration of 10 mM, or of 20 mM, or of 30 mM, or of 40 mM, or of 50 mM, or of 60 mM, or of 70 mM, or of 80 mM, or of 90 mM, or of 100 mM, or of 150 mM, or of 200 mM.

In a preferred embodiment, the composition according to the invention comprises phosphate in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 110 mM, or of about 120 mM, or of about 130 mM, or of about 140 mM, or of about 150 mM, or of about 160 mM, or of about 170 mM, or of about 180 mM, or of about 190 mM, or of about 200 mM.

In a preferred embodiment, the composition according to the invention comprises phosphate in a concentration of 10 mM, or of 20 mM, or of 30 mM, or of 40 mM, or of 50 mM, or of 60 mM, or of 70 mM, or of 80 mM, or of 90 mM, or of 100 mM, or of 110 mM, or of 120 mM, or of 130 mM, or of 140 mM, or of 150 mM, or of 160 mM, or of 170 mM, or of 180 mM, or of 190 mM, or of 200 mM.

In a preferred embodiment, the composition according to the invention comprises about 2 mg/ml of the polypeptides according to the invention and TRIS in a concentration of 10 mM, or of 20 mM, or of 30 mM, or of 40 mM, or of 50 mM, or of 60 mM, or of 70 mM, or of 80 mM, or of 90 mM, or of 100 mM, or of 150 mM, or of 200 mM, or of 250 mM, or of 300 mM and phosphate in a concentration of 10 mM, or of 20 mM, or of 30 mM, or of 40 mM, or of 50 mM, or of 60 mM, or of 70 mM, or of 80 mM, or of 90 mM, or of 100 mM, or of 150 mM, or of 200 mM.

In a preferred embodiment, the composition according to the invention comprises about 2 mg/ml of the polypeptides according to the invention and phosphate in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 110 mM, or of about 120 mM, or of about 130 mM, or of about 140 mM, or of about 150 mM, or of about 160 mM, or of about 170 mM, or of about 180 mM, or of about 190 mM, or of about 200 mM.

In a preferred embodiment, the composition according to the invention comprises about 2 mg/ml of the polypeptides according to the invention and phosphate in a concentration of 10 mM, or of 20 mM, or of 30 mM, or of 40 mM, or of 50 mM, or of 60 mM, or of 70 mM, or of 80 mM, or of 90 mM, or of 100 mM, or of 110 mM, or of 120 mM, or of 130 mM, or of 140 mM, or of 150 mM, or of 160 mM, or of 170 mM, or of 180 mM, or of 190 mM, or of 200 mM.

In a preferred embodiment, the composition according to the invention comprises about 2 mg/ml of the polypeptides according to the invention and TRIS in a concentration of about 100 mM and phosphate in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 110 mM, or of about 120 mM, or of about 130 mM, or of about 140 mM, or of about 150 mM, or of about 160 mM, or of about 170 mM, or of about 180 mM, or of about 190 mM, or of about 200 mM.

In a preferred embodiment, the composition according to the invention comprises about 2 mg/ml of the polypeptides according to the invention and TRIS in a concentration of about 100 mM and phosphate in a concentration of 10 mM, or of 20 mM, or of 30 mM, or of 40 mM, or of 50 mM, or of 60 mM, or of 70 mM, or of 80 mM, or of 90 mM, or of 100 mM, or of 110 mM, or of 120 mM, or of 130 mM, or of 140 mM, or of 150 mM, or of 160 mM, or of 170 mM, or of 180 mM, or of 190 mM, or of 200 mM.

In a preferred embodiment, the composition according to the invention comprises about 2 mg/ml of the polypeptides according to the invention and phosphate in a concentration of about 50 mM and TRIS in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 150 mM, or of about 200 mM, or of about 250 mM, or of about 300 mM and phosphate in a concentration of about 10 mM, or of about 20 mM, or of about 30 mM, or of about 40 mM, or of about 50 mM, or of about 60 mM, or of about 70 mM, or of about 80 mM, or of about 90 mM, or of about 100 mM, or of about 150 mM, or of about 200 mM.

In a preferred embodiment, the composition according to the invention comprises about 2 mg/ml of the polypeptides according to the invention and phosphate in a concentration of about 50 mM and TRIS in a concentration of 10 mM, or of 20 mM, or of 30 mM, or of 40 mM, or of 50 mM, or of 60 mM, or of 70 mM, or of 80 mM, or of 90 mM, or of 100 mM, or of 150 mM, or of 200 mM, or of 250 mM, or of 300 mM and phosphate in a concentration of 10 mM, or of 20 mM, or of 30 mM, or of 40 mM, or of 50 mM, or of 60 mM, or of 70 mM, or of 80 mM, or of 90 mM, or of 100 mM, or of 150 mM, or of 200 mM.

In a preferred embodiment, the pH of the composition according to the invention is within a range from about 5.0 to about 7.0, or within a range from about 5.0 to about 6.5. Particularly preferably, the pH of the composition according to the invention is 6.0. Preferably, the pH of the composition according to the invention is adjusted using HCl.

In a further embodiment, the composition according to the invention additionally comprises a wetting agent. Examples of wetting agents are non-ionic wetting agents such as polysorbates (e.g. polysorbate 20 or 80); poloxamers (e.g. poloxamer 188); Triton; sodium octyl glycoside; lauryl, myristyl, linoleyl, or stearyl sulphobetaine; lauroylsarcosine, myristoylsarcosine, linoleoylsarcosine, or stearoylsarcosine; linoleyl, myristyl, or cetyl betaine; lauroamidopropyl, cocamidopropyl, linoleamidopropyl, myristamidopropyl, palmitamidopropyl, or isostearamidopropyl betaine; polyethylene glycol; polypropylene glycol; and copolymers of ethylene and propylene glycol (e.g. Pluronics, PF68). In a preferred embodiment, the wetting agent is polysorbate 80.

In a further embodiment, the composition according to the invention comprises a wetting agent in a concentration of from 0.002% to 0.1%, preferably from 0.04% to 0.1%.

In a preferred embodiment, the composition according to the invention comprises polysorbate 80 in a concentration of from 0.002% to 0.1%, preferably from 0.04% to 0.1%. Particularly preferably, the composition according to the invention comprises polysorbate 80 in a concentration of 0.04%.

In a further embodiment, the composition according to the invention additionally comprises a lyoprotectant. In a further embodiment, the composition according to the invention additionally comprises a sugar or a sugar alcohol as lyoprotectant. The lyoprotectant is preferably trehalose or trehalose dihydrate. In a preferred embodiment, the composition according to the invention comprises the lyoprotectant in a concentration of from 2% to 10%, particularly preferably 4%.

In a preferred embodiment, the composition according to the invention comprises trehalose in a concentration of from 2% to 10%, particularly preferably 4%.

In a particularly preferred embodiment, the composition according to the invention comprises trehalose dihydrate in a concentration of from 2% to 10%, particularly preferably 4%.

Particularly preferably, the composition according to the invention comprises from about 0.5 µg/ml to about 2 mg/ml of the PSMA-BiTE1 molecules and TRIS in a concentration of from about 50 mM to about 200 mM, phosphate in a concentration of from about 20 mM to about 100 mM, polysorbate 80 in a concentration of 0.04% and trehalose dihydrate in a concentration of 4%, and the pH is 6.0.

Particularly preferably, the composition according to the invention comprises from about 0.5 µg/ml to about 2 mg/ml of the PSMA-BiTE1 molecules and TRIS in a concentration of from about 50 mM to about 200 mM, phosphate in a concentration of about 50 mM, polysorbate 80 in a concentration of 0.04% and trehalose dihydrate in a concentration of 4%, and the pH is 6.0.

Particularly preferably, the composition according to the invention comprises from about 0.5 µg/ml to about 2 mg/ml of the PSMA-BiTE1 molecules and TRIS in a concentration of about 100 mM, phosphate in a concentration of from about 20 mM to about 100 mM, polysorbate 80 in a concentration of 0.04% and trehalose dihydrate in a concentration of 4%, and the pH is 6.0.

Particularly preferably, the composition according to the invention comprises from about 50 µg/ml to about 2 mg/ml of the PSMA-BiTE1 molecules and TRIS in a concentration of about 100 mM, phosphate in a concentration of about 50 mM, polysorbate 80 in a concentration of 0.04% and trehalose dihydrate in a concentration of 4%, and the pH is 6.0.

Particularly preferably, the composition according to the invention comprises from about 50 µg/ml to about 1 mg/ml of the PSMA-BiTE1 molecules and TRIS in a concentration of about 100 mM, phosphate in a concentration of about 50 mM, polysorbate 80 in a concentration of 0.04% and trehalose dihydrate in a concentration of 4%, and the pH is 6.0.

Particularly preferably, the composition according to the invention comprises from about 100 µg/ml to about 500 µg/ml of the PSMA-BiTE1 molecules and TRIS in a concentration of about 100 mM, phosphate in a concentration of about 50 mM, polysorbate 80 in a concentration of 0.04% and trehalose dihydrate in a concentration of 4%, and the pH is 6.0.

Particularly preferably, the composition according to the invention comprises about 2 mg/ml of the PSMA-BiTE1 molecules and TRIS in a concentration of about 100 mM, phosphate in a concentration of about 50 mM, polysorbate 80 in a concentration of 0.04% and trehalose dihydrate in a concentration of 4%, and the pH is 6.0.

Particularly preferably, the composition according to the invention comprises about 2 mg/ml of the PSMA-BiTE1 molecules and TRIS in a concentration of about 100 mM, $Na_2HPO_4$ in a concentration of about 50 mM, polysorbate 80 in a concentration of 0.04% and trehalose dihydrate in a concentration of 4%, and the pH is 6.0.

Preferably, the composition according to the invention comprises from about 0.5 µg/ml to about 2 mg/ml of the PSMA-BiTE1 molecules and TRIS in a concentration of from about 50 mM to about 200 mM, phosphate in a concentration of from about 20 mM to about 100 mM, polysorbate 80 in a concentration of 0.04% and trehalose in a concentration of 4%, and the pH is 6.0.

Preferably, the composition according to the invention comprises from about 0.5 µg/ml to about 2 mg/ml of the PSMA-BiTE1 molecules and TRIS in a concentration of from about 50 mM to about 200 mM, phosphate in a concentration of about 50 mM, polysorbate 80 in a concentration of 0.04% and trehalose in a concentration of 4%, and the pH is 6.0.

Preferably, the composition according to the invention comprises from about 0.5 µg/ml to about 2 mg/ml of the PSMA-BiTE1 molecules and TRIS in a concentration of about 100 mM, phosphate in a concentration of from about 20 mM to about 100 mM, polysorbate 80 in a concentration of 0.04% and trehalose in a concentration of 4%, and the pH is 6.0.

Preferably, the composition according to the invention comprises from about 50 µg/ml to about 2 mg/ml of the PSMA-BiTE1 molecules and TRIS in a concentration of about 100 mM, phosphate in a concentration of about 50 mM, polysorbate 80 in a concentration of 0.04% and trehalose in a concentration of 4%, and the pH is 6.0.

Preferably, the composition according to the invention comprises from about 50 µg/ml to about 1 mg/ml of the PSMA-BiTE1 molecules and TRIS in a concentration of about 100 mM, phosphate in a concentration of about 50 mM, polysorbate 80 in a concentration of 0.04% and trehalose in a concentration of 4%, and the pH is 6.0.

Preferably, the composition according to the invention comprises from about 100 µg/ml to about 500 µg/ml of the PSMA-BiTE1 molecules and TRIS in a concentration of about 100 mM, phosphate in a concentration of about 50 mM, polysorbate 80 in a concentration of 0.04% and trehalose in a concentration of 4%, and the pH is 6.0.

Preferably, the composition according to the invention comprises about 2 mg/ml of the PSMA-BiTE1 molecules and TRIS in a concentration of about 100 mM, phosphate in a concentration of about 50 mM, polysorbate 80 in a concentration of 0.04% and trehalose in a concentration of 4%, and the pH is 6.0.

Preferably, the composition according to the invention comprises about 2 mg/ml of the PSMA-BiTE1 molecules and TRIS in a concentration of about 100 mM, $Na_2HPO_4$ in a concentration of about 50 mM, polysorbate 80 in a concentration of 0.04% and trehalose in a concentration of 4%, and the pH is 6.0.

Indicated concentrations in per cent (%) refer to the concentration by mass (mass/volume).

In addition, the compositions according to the invention can contain yet further pharmaceutically acceptable additives (Remington's Pharmaceutical Sciences; 18th edition, Mack Publishing Co., Easton, Pa., USA). Such additives are, for example, preservatives or antioxidants. Antioxidants which can be used are, for example, ascorbate, methionine, vitamin E, or sodium metabisulphite. Preservatives are, for example, substances which suppress or slow the growth of microorganisms. Such a substance is, for example, thiomersal.

One embodiment of the present invention is a solids mixture which is produced by lyophilization of the composition according to the invention, or is obtainable at least by lyophilization of said composition.

A preferred embodiment of the present invention is a lyophilisate obtainable by freeze-drying a composition according to the invention.

A preferred embodiment of the present invention is a lyophilisate produced by freeze-drying a composition according to the invention as per the protocol described in example 16.

In a further embodiment, the composition according to the invention is provided by reconstituting the lyophilized solids mixture by dissolution in a suitable liquid medium.

In a preferred embodiment, the composition according to the invention is provided by reconstituting the lyophilized solids mixture by dissolution in water, preferably sterile water.

The invention further provides a product which contains one of the compositions according to the invention and preferably also instructions for use. In one embodiment, the product comprises a container which contains one of the above-listed compositions. Useful containers are, for example, bottles, vials, tubes or syringes. The containers can, for example, be composed of glass or plastic. Syringes can comprise an injection needle composed, for example, of metal.

In one embodiment, the container is a syringe. In a further embodiment, the syringe is contained in an injection device. In a preferred embodiment, the injection device is an auto-injector. An auto-injector can be described as an injection instrument which, after activation, administers its contents without additional handling by the patient or another person. In the present invention, administration is preferably subcutaneous.

The compositions according to the invention exhibit increased stability and significantly increased bioavailability compared to the formulations available in the prior art for BiTE molecules. Owing to this property profile, the compositions according to the invention are especially suitable for parenteral administration. Parenteral administration includes, inter alia, intravenous injection or infusion, intra-arterial injection or infusion (into an artery), intra-muscular injection, intra-thecal injection, subcutaneous injection, intra-peritoneal injection or infusion, intra-osseous administration or injection into a tissue. The compositions according to the invention are especially suitable for subcutaneous administration. One embodiment of the composition according to the invention is characterized in that the bioavailability of the polypeptide after subcutaneous administration of the composition is >60%; preferably, this is the bioavailability in a cynomolgus monkey.

The compositions according to the invention have valuable pharmacological properties and can be used for the prevention and treatment of diseases in humans and animals.

The compositions according to the invention are suitable in general for the treatment of hyper-proliferative diseases in humans and in mammals. Hyper-proliferative diseases, for the treatment of which it is possible to use the compositions according to the invention, belong in particular to the group of cancer and tumour diseases. In the context of the present invention, these are understood to mean especially the following diseases, but without any limitation thereto: mammary carcinomas and mammary tumours (ductal and lobular forms, also in situ), tumours of the respiratory tract (parvicellular and non-parvicellular carcinoma, bronchial carcinoma), cerebral tumours (e.g. of the brain stem and of the hypothalamus, astrocytoma, medulloblastoma, ependymoma and neuro-ectodermal and pineal tumours), tumours of the digestive organs (oesophagus, stomach, gall bladder, small intestine, large intestine, rectum), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity), skin tumours (squamous cell carcinoma, Kaposi's sarcoma, malignant melanoma, Merkel cell skin cancer and non-melanomatous skin cancer), tumours of soft tissue (inter alia soft tissue sarcomas, osteosarcomas, malignant fibrous histiocytomas, lymphosarcomas and rhabdomyosarcomas), tumours of the eyes (inter alia intraocular melanoma and retinoblastoma), tumours of the endocrine and exocrine glands (e.g. thyroid and parathyroid glands, pancreas and salivary gland), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative blood diseases in solid form and as circulating blood cells, such as lymphomas, leukaemias and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

Preferred diseases, for the treatment of which it is possible to use the compositions according to the invention, are carcinomas and/or metastases which express the PSMA antigen.

A particularly preferred disease, for the treatment of which it is possible to use the compositions according to the invention, is selected from the group consisting of prostate carcinoma, bone metastases of the prostate carcinoma and soft tissue metastases of the prostate carcinoma.

A further particularly preferred disease, for the treatment of which it is possible to use the compositions according to the invention, is prostate carcinoma.

These well described diseases in humans can also occur with a comparable aetiology in other mammals and can be treated there with the compositions of the present invention.

In the context of this invention, the term "treatment" or "treat" is used in the conventional sense and means attending to, caring for and nursing a patient with the aim of combating, reducing, attenuating or alleviating a disease or health abnormality, and improving the quality of life impaired by this disease, as, for example, in the event of a cancer.

The present invention thus further provides for the use of the compositions according to the invention for the treatment and/or prevention of diseases, more particularly the above-mentioned diseases.

The present invention further provides for the use of the compositions according to the invention for producing a medicinal product for the treatment and/or prevention of diseases, more particularly the above-mentioned diseases.

The present invention further provides for the use of the compositions according to the invention in a method for treating and/or preventing diseases, more particularly the above-mentioned diseases.

The present invention further provides a method for treating and/or preventing diseases, more particularly the above-mentioned diseases, using an effective amount of one of the compositions according to the invention.

In a preferred embodiment, the treatment and/or prevention is parenteral administration of the composition according to the invention. Particular preference is given to subcutaneous administration.

The compositions according to the invention can be used alone or, if required, in combination with one or more other pharmacologically active substances, provided that this combination does not lead to undesirable and unacceptable side effects. The present invention therefore further provides medicinal products containing at least one of the compositions according to the invention and one or more further active ingredients, especially for the treatment and/or prevention of the above-mentioned diseases. For example, the compounds of the present invention can be combined with known anti-hyper-proliferative, cytostatic or cytotoxic substances for the treatment of cancer diseases.

The invention further provides for the use of the above-mentioned compositions in a therapeutic method, the composition being suitable for parenteral forms of administration, such as intravenous injection or infusion, intra-arterial injection or infusion (into an artery), intra-muscular injection, intra-thecal injection, subcutaneous injection, intra-peritoneal injection or infusion, intra-osseous administration or injection into a tissue.

The invention further provides for the use of the above-mentioned compositions in a method for therapeutically treating cell-proliferative diseases of the prostate.

The invention further provides for the use of the above-mentioned compositions in a method for therapeutically treating cell-proliferative diseases of the prostate, the composition being suitable for subcutaneous administration.

The invention further provides for the use of the above-mentioned compositions in a method for therapeutically treating cell-proliferative diseases of the prostate, the composition being administered by subcutaneous administration.

The invention further provides a method for stabilizing polypeptides, comprising the production of one of the above-mentioned compositions, which contains, in addition to the polypeptides, at least TRIS and phosphate and has a pH of 6.0.

The invention further provides a kit which comprises the above-mentioned compositions.

Preferred compounds in the context of the present invention are pharmaceutical compounds.

EMBODIMENTS

One embodiment of the present invention comprises a liquid pharmaceutical composition comprising a polypeptide, TRIS and phosphate, the polypeptide comprising two scFv antibody binding domains, the first scFv binding domain being able to bind to human CD3 epsilon.

In a further embodiment of the composition, the second binding domain of the polypeptide can bind to a cell surface antigen.

In a further embodiment of the composition, the polypeptide comprises a second binding domain which can bind to a surface antigen of a cancer cell.

In a further embodiment, the surface antigen to which the second binding domain of the polypeptide can bind is prostate-specific membrane antigen (PSMA).

In a further embodiment of the composition, the polypeptide has the arrangement (VH-VL) binding domain 2-(VH-VL) binding domain 1.

In a further embodiment of the composition, the first binding domain of the polypeptide comprises the amino acid sequence reproduced in SEQ ID NO: 5.

In a further embodiment of the composition, the second, PSMA-binding binding domain of the polypeptide comprises the amino acid sequence reproduced in SEQ ID NO: 6.

In a further embodiment, the composition comprises a polypeptide, TRIS and phosphate, the polypeptide comprising the amino acid sequence reproduced in SEQ ID NO: 7.

In a further embodiment, the composition comprises a polypeptide, TRIS and phosphate, the polypeptide comprising the amino acid sequence reproduced in SEQ ID NO: 8.

In a further embodiment, the composition contains the polypeptide in a concentration of from 0.5 µg/ml to 5 mg/ml.

In a further embodiment, the composition contains the polypeptide in a concentration of from 0.5 µg/ml to 3.5 mg/ml.

In a further embodiment, the composition contains the polypeptide in a concentration of from 0.5 µg/ml to 3.0 mg/ml.

In a further embodiment, the composition contains the polypeptide in a concentration of from 0.5 µg/ml to 2.5 mg/ml.

In a further embodiment, the composition contains the polypeptide in a concentration of from 0.5 µg/ml to 2.0 mg/ml.

In a further embodiment, the composition contains the polypeptide in a concentration of from 0.5 µg/ml to 1.8 mg/ml.

In a further embodiment, the composition contains the polypeptide in a concentration of from 0.5 µg/ml to 1.5 mg/ml.

In a further embodiment, the composition contains the polypeptide in a concentration of from 0.5 µg/ml to 0.35 mg/ml.

In a further embodiment, the composition contains the polypeptide in a concentration of from 0.5 µg/ml to 0.3 mg/ml.

In a further embodiment, the composition contains the polypeptide in a concentration of from 0.5 µg/ml to 0.25 mg/ml.

In a further embodiment, the composition contains the polypeptide in a concentration of from 0.5 µg/ml to 0.2 mg/ml.

In a further embodiment, the composition comprises the PSMA-BiTE1 in a concentration of from 50 µg/ml to 1 mg/ml.

In a further embodiment, the composition comprises the PSMA-BiTE1 in a concentration of from 50 µg/ml to 500 µg/ml.

In a further embodiment, the composition comprises the PSMA-BiTE1 in a concentration of from 100 µg/ml to 500 µg/ml.

In a further embodiment, the composition contains the polypeptide in a concentration of about 2 mg/ml.

In a further embodiment, the composition contains TRIS in a concentration of from about 50 mM to about 200 mM and phosphate in a concentration of from about 20 mM to about 100 mM.

In a further embodiment, the composition contains 100 mM TRIS and 50 mM phosphate.

In a further embodiment, the pH of the composition is within a range from about 5.0 to about 7.0.

In a further embodiment, the pH of the composition is within a range from about 5.0 to about 6.5.

In a further embodiment, the pH of the composition is within a range from about 5.5 to about 6.5.

In a further embodiment, the pH of the composition is about 6.0.

In a further embodiment, the pH of the composition is adjusted using hydrochloric acid.

In a further embodiment, the composition additionally contains a wetting agent.

In a further embodiment, the wetting agent is polysorbate 80.

In a further embodiment, the composition additionally contains from 0.002% to 0.1% polysorbate 80.

In a further embodiment, the composition additionally contains from 0.04% to 0.1% polysorbate 80.

In a further embodiment, the composition additionally contains 0.04% polysorbate 80.

In a further embodiment, the composition additionally contains a lyoprotectant.

In a further embodiment, the composition contains trehalose or preferably trehalose dihydrate as lyoprotectant.

In a further embodiment, the composition additionally contains from 4% to 10% trehalose or preferably from 4% to 10% trehalose dihydrate.

In a further embodiment, the composition additionally contains about 4% trehalose or preferably additionally about 4% trehalose dihydrate.

In a preferred embodiment, the composition has a pH of 6 and comprises from 50 µg/ml to 1 mg/ml PSMA-BiTE1, 100 mM TRIS, 50 mM phosphate, 0.04% polysorbate 80 and 4% trehalose dihydrate.

In a preferred embodiment, the composition has a pH of 6 and comprises from 50 µg/ml to 500 µg/ml PSMA-BiTE1, 100 mM TRIS, 50 mM phosphate, 0.04% polysorbate 80 and 4% trehalose dihydrate.

In a preferred embodiment, the composition has a pH of 6 and comprises from 50 µg/ml to 500 µg/ml PSMA-BiTE1, 100 mM TRIS, 50 mM $Na_2HPO_4$, 0.04% polysorbate 80 and 4% trehalose dihydrate.

In a further embodiment, the composition has a pH of 6 and comprises from 50 µg/ml to 1 mg/ml PSMA-BiTE1, 100 mM TRIS, 50 mM phosphate, 0.04% polysorbate 80 and 4% trehalose.

In a further embodiment, the composition has a pH of 6 and comprises from 50 µg/ml to 500 µg/ml PSMA-BiTE1, 100 mM TRIS, 50 mM phosphate, 0.04% polysorbate 80 and 4% trehalose.

In a further embodiment, the composition has a pH of 6 and comprises from 50 µg/ml to 500 µg/ml PSMA-BiTE1, 100 mM TRIS, 50 mM $Na_2HPO_4$, 0.04% polysorbate 80 and 4% trehalose.

In a preferred embodiment of the composition, the polypeptide has a bioactivity of at least 90% and preferably at least 96% (preferably ascertained by cell-based activity assay as described in example 21) following lyophilization and subsequent reconstitution and storage (7 days at 2-8° C. and subsequently 16 hours at 20° C.+−5° C., as described in example 21).

In a preferred embodiment of the composition, the polypeptide has a bioactivity of at least 90% and preferably at least 96% (preferably ascertained by cell-based activity assay as described in example 21) following lyophilization and storage for 3 months or 12 months.

In a preferred embodiment of the composition, the polypeptide has a bioactivity of at least 97% (preferably ascertained by cell-based activity assay as described in example 21) following lyophilization and storage for 3 months at 6° C. or 12 months at 6° C.

In a preferred embodiment of the composition, the polypeptide has a monomer content (SEC) of more than 96% (preferably ascertained as per example 18a) following the action of shear stress resulting from injection.

In a preferred embodiment of the composition, the polypeptide has a dimer and multimer content (SEC) of not more than 4% (preferably ascertained as per example 18a) following the action of shear stress resulting from slow or rapid injection using a needle.

In a preferred embodiment of the composition, the polypeptide has a dimer and multimer content (SEC) of not more than 4% (preferably ascertained as per example 18a) following the action of shear stress resulting from slow or rapid injection using a needle (gauge: 30 G; needle length: 13 mm).

One embodiment of the present invention comprises a solids mixture obtainable by lyophilization of the liquid composition.

In a further embodiment, the composition is reconstituted by dissolving the lyophilized solids mixture according to the invention in a suitable liquid medium.

In a further embodiment, the bioavailability of the polypeptide following subcutaneous administration of the composition is >60%.

In a further embodiment, the composition is used in a therapeutic method.

In a further embodiment, the composition is used in a therapeutic method, said method comprising parenteral administration of the composition.

In a further embodiment, the composition is used in a method for therapeutically treating hyper-proliferative diseases.

In a further embodiment, the composition is used in a method for therapeutically treating hyper-proliferative diseases of the prostate.

In a further embodiment, the composition is used in a method for therapeutically treating hyper-proliferative diseases of the prostate, the method comprising subcutaneous administration of the composition.

In a further embodiment, the present invention comprises a method for stabilizing polypeptides, comprising the production of a composition which contains, in addition to the polypeptides, at least TRIS and phosphate and has a pH of 6.0.

In a further embodiment, the present invention comprises a kit comprising the above-described composition.

Preferred embodiments are
1. A liquid pharmaceutical composition comprising a polypeptide, TRIS and phosphate, the polypeptide comprising two scFv antibody binding domains, the first scFv binding domain being able to bind to human CD3 epsilon.
2. A composition according to embodiment 1, characterized in that the second binding domain of the polypeptide can bind to a cell surface antigen.
3. A composition according to embodiment 2, characterized in that the polypeptide comprises a second binding domain which can bind to a surface antigen of a cancer cell.
4. A composition according to either of embodiments 2 and 3, characterized in that the surface antigen is prostate-specific membrane antigen (PSMA).
5. A composition according to any of the preceding embodiments, characterized in that the polypeptide has the arrangement (VH-VL)$_{Binding\ domain\ 2}$-(VH-VL)$_{Binding\ domain\ 1}$.
6. A composition according to any of the preceding embodiments, characterized in that the first binding domain of the polypeptide comprises the amino acid sequence reproduced in SEQ ID NO: 5.
7. A composition according to any of the preceding embodiments, characterized in that the second, PSMA-binding binding domain of the polypeptide comprises the amino acid sequence reproduced in SEQ ID NO: 6.
8. A liquid pharmaceutical composition comprising a polypeptide, TRIS and phosphate, the polypeptide comprising the amino acid sequence reproduced in SEQ ID NO: 7.
9. A liquid pharmaceutical composition comprising a polypeptide, TRIS and phosphate, the polypeptide comprising the amino acid sequence reproduced in SEQ ID NO: 8.
10. A composition according to any of the preceding embodiments, characterized in that the composition contains the polypeptide in a concentration of from 0.5 µg/ml to 5 mg/ml.
11. A composition according to any of the preceding embodiments, characterized in that the composition contains the polypeptide in a concentration of from 0.5 µg/ml to 3.5 mg/ml.
12. A composition according to any of the preceding embodiments, characterized in that the composition contains the polypeptide in a concentration of from 0.5 µg/ml to 3.0 mg/ml.
13. A composition according to any of the preceding embodiments, characterized in that the composition contains the polypeptide in a concentration of from 0.5 µg/ml to 2.5 mg/ml.
14. A composition according to any of the preceding embodiments, characterized in that the composition contains the polypeptide in a concentration of from 0.5 µg/ml to 2.0 mg/ml.
15. A composition according to any of the preceding embodiments, characterized in that the composition contains the polypeptide in a concentration of from 0.5 µg/ml to 1.8 mg/ml.
16. A composition according to any of the preceding embodiments, characterized in that the composition contains the polypeptide in a concentration of from 0.5 µg/ml to 1.5 mg/ml.
17. A composition according to any of the preceding embodiments, characterized in that the composition contains the polypeptide in a concentration of from 0.5 µg/ml to 0.35 mg/ml.
18. A composition according to any of the preceding embodiments, characterized in that the composition contains the polypeptide in a concentration of from 0.5 µg/ml to 0.3 mg/ml.
19. A composition according to any of the preceding embodiments, characterized in that the composition contains the polypeptide in a concentration of from 0.5 µg/ml to 0.25 mg/ml.
20. A composition according to any of the preceding embodiments, characterized in that the composition contains the polypeptide in a concentration of from 0.5 µg/ml to 0.2 mg/ml.
21. A composition according to any of the preceding embodiments, characterized in that the composition comprises the PSMA-BiTE1 in a concentration of from 50 µg/ml to 1 mg/ml.
22. A composition according to any of the preceding embodiments, characterized in that the composition comprises the PSMA-BiTE1 in a concentration of from 50 µg/ml to 500 µg/ml.
23. A composition according to any of the preceding embodiments, characterized in that the composition comprises the PSMA-BiTE1 in a concentration of from 100 µg/ml to 500 µg/ml.
24. A composition according to any of the preceding embodiments, characterized in that the composition contains the polypeptide in a concentration of about 2 mg/ml.
25. A composition according to any of the preceding embodiments, characterized in that the composition contains TRIS in a concentration of from about 50 mM to about 200 mM and phosphate in a concentration of from about 20 mM to about 100 mM.
26. A composition according to any of the preceding embodiments, characterized in that the composition contains 100 mM TRIS and 50 mM phosphate.
27. A composition according to any of the preceding embodiments, characterized in that the pH of the composition is within a range from about 5.0 to about 7.0.
28. A composition according to any of the preceding embodiments, characterized in that the pH of the composition is within a range from about 5.0 to about 6.5.

29. A composition according to any of the preceding embodiments, characterized in that the pH of the composition is within a range from about 5.5 to about 6.5.
30. A composition according to any of the preceding embodiments, characterized in that the pH of the composition is about 6.0.
31. A composition according to any of the preceding embodiments, characterized in that the pH of the composition is adjusted using hydrochloric acid.
32. A composition according to any of the preceding embodiments, characterized in that the composition additionally contains a wetting agent.
33. A composition according to embodiment 32, characterized in that the wetting agent is polysorbate 80.
34. A composition according to any of the preceding embodiments, characterized in that the composition additionally contains from 0.002% to 0.1% polysorbate 80.
35. A composition according to any of the preceding embodiments, characterized in that the composition additionally contains from 0.04% to 0.1% polysorbate 80.
36. A composition according to any of the preceding embodiments, characterized in that the composition additionally contains 0.04% polysorbate 80.
37. A composition according to any of the preceding embodiments, characterized in that the composition additionally contains a lyoprotectant. The composition contains preferably 2-10% of a lyoprotectant, particularly preferably 4%.
38. A composition according to embodiment 37, characterized in that the lyoprotectant is trehalose. The lyoprotectant is preferably trehalose dihydrate.
39. A composition according to any of the preceding embodiments, characterized in that the composition additionally contains from 4% to 10% trehalose dihydrate.
40. A composition according to any of the preceding embodiments, characterized in that the composition additionally contains about 4% trehalose dihydrate.
41. A composition according to any of the preceding embodiments, characterized in that the composition has a pH of 6 and comprises from 50 µg/ml to 1 mg/ml PSMA-BiTE1, 100 mM TRIS, 50 mM phosphate, 0.04% polysorbate 80 and 4% trehalose dihydrate.
42. A composition according to any of the preceding embodiments, characterized in that the composition has a pH of 6 and comprises from 50 µg/ml to 500 µg/ml PSMA-BiTE1, 100 mM TRIS, 50 mM phosphate, 0.04% polysorbate 80 and 4% trehalose dihydrate.
43. A composition according to any of the preceding embodiments, characterized in that the composition has a pH of 6 and comprises 2 mg/ml PSMA-BiTE1, 100 mM TRIS, 50 mM $Na_2HPO_4$, 0.04% polysorbate 80 and 4% trehalose dihydrate.
44. A solids mixture obtainable by lyophilization of a liquid composition according to any of the preceding embodiments.
45. A liquid pharmaceutical composition, characterized in that the composition is reconstituted by dissolving a lyophilized solids mixture according to embodiment 44 in a suitable liquid medium.
46. A composition according to any of the preceding embodiments, wherein the polypeptide has a bioactivity of at least 90% and preferably at least 96% (preferably ascertained by cell-based activity assay as described in example 21) following lyophilization and subsequent reconstitution and storage (7 days at 2-8° C. and subsequently 16 hours at 20° C.+−5° C., as described in example 21).
47. A composition according to any of the preceding embodiments, wherein the polypeptide has a bioactivity of at least 90% and preferably at least 96% (preferably ascertained by cell-based activity assay as described in example 21) following lyophilization and storage for 3 months or 12 months.
48. A composition according to any of the preceding embodiments, wherein the polypeptide has a bioactivity of at least 97% (preferably ascertained by cell-based activity assay as described in example 21) following lyophilization and storage for 3 months at 6° C. or 12 months at 6° C.
49. A composition according to any of the preceding embodiments, wherein the polypeptide has a monomer content (SEC) of more than 96% (preferably ascertained as per example 18a) following the action of shear stress resulting from injection.
50. A composition according to any of the preceding embodiments, wherein the polypeptide has a dimer and multimer content (SEC) of not more than 4% (preferably ascertained as per example 18a) following the action of shear stress resulting from slow or rapid injection using a needle.
51. A composition according to any of the preceding embodiments, wherein the polypeptide has a dimer and multimer content (SEC) of not more than 4% (preferably ascertained as per example 18a) following the action of shear stress resulting from slow or rapid injection using a needle (gauge: 30 G; needle length: 13 mm).
52. A composition according to any of the preceding embodiments, characterized in that the bioavailability of the polypeptide following subcutaneous administration of the composition is >60%.
53. A composition according to any of the preceding embodiments for use in a therapeutic method.
54. A composition according to any of the preceding embodiments for use in a therapeutic method, said method comprising parenteral administration of the composition.
55. A composition according to any of the preceding embodiments for use in a method for therapeutically treating hyper-proliferative diseases.
56. A composition according to any of the preceding embodiments for use in a method for therapeutically treating hyper-proliferative diseases of the prostate.
57. A composition according to any of the preceding embodiments for use in a method for therapeutically treating hyper-proliferative diseases of the prostate, the method comprising subcutaneous administration of the composition.
58. A method for stabilizing polypeptides according to at least one of embodiments 1 to 9, comprising the production of a composition which contains, in addition to the polypeptides, at least TRIS and phosphate and has a pH of 6.0.
59. A kit comprising the composition according to any of embodiments 1-57.
60. A composition according to any of the preceding embodiments, wherein the liquid pharmaceutical composition is an aqueous pharmaceutical composition, preferably a sterile aqueous pharmaceutical composition.
61. Syringe containing a composition according to any of the preceding embodiments.

EXAMPLES

Example 1

Buffer Screening in Order to Improve the Thermal Stability of the PSMA-BiTE1 Molecules Differential scanning fluorimetry (DSF) was used to measure the mean melting point ($T_{m1}$) of the PSMA-BiTE1 protein domain with the lowest molecular weight in different buffer systems. It is a measure of the stability of the examined protein in the various buffer systems: the greater the $T_m$ value, the greater, too, the thermal stability of the protein. The greater the thermal stability of a protein, the better its suitability for producing stable pharmaceutical formulations.

For the buffer screening, standard buffers in a pH range from pH 5.0 to 8.0 were used. The PSMA-BiTE1 concentration of the formulations produced was about 0.2 mg/ml. The mean melting point was ascertained by the DSF method.

TABLE 1

PSMA-BITE1 (0.2 mg/ml) in various buffer systems (50 mM)

| pH | Na$_2$HPO$_4$ Tm1 [° C.] | Citrate Tm1 [° C.] | Histidine Tm1 [° C.] | Glycine Tm1 [° C.] | Lysine Tm1 [° C.] |
|---|---|---|---|---|---|
| 5.0 | 61.2 | 63.6 | — | — | — |
| 5.5 | 63.5 | 63.1 | 60.8 | — | — |
| 6.0 | 63.4 | 63.5 | 61.4 | 60.2 | 61.6 |
| 6.5 | 63.8 | 64.6 | 60.7 | 58.7 | 61.5 |
| 7.0 | 63.3 | — | 60.4 | 60.7 | 61.4 |
| 7.5 | 63.1 | — | 57.7 | 61.4 | 61.4 |
| 8.0 | 63.0 | — | 59.3 | — | — |

The buffer systems based on citrate and Na$_2$HPO$_4$ exhibited a positive effect with respect to increasing the melting point of the PSMA-BiTE1 protein domain. The positive effects of citrate and Na$_2$HPO$_4$ were followed up in further experiments.

Tris(hydroxymethyl)aminomethane (TRIS)-based buffers alone did not lead to a distinct increase in the protein melting point (table 2).

TABLE 2

PSMA-BiTE1 (0.2 mg/ml) in various buffer systems (50 mM) (continuation of tab. 1)

| pH | HEPES Tm1 [° C.] | TRIS Tm1 [° C.] | MOPS Tm1 [° C.] | Acetate Tm1 [° C.] |
|---|---|---|---|---|
| 6.5 | — | 61.7 | 62.5 | 61.9 |
| 7.0 | 62.2 | 61.4 | 61.8 | — |
| 7.5 | 61.4 | — | 62.6 | — |
| 8.0 | 61.4 | — | 62.4 | — |

Like table 1, table 2 also shows the mean melting point (Tm), as ascertained by differential scanning fluorimetry, of the PSMA-BiTE1 protein domain with the lowest molecular weight in different buffer systems. The Tm values were between 57.7° C. and 64.6° C. Through the combination of various buffer systems, it was not possible to attain higher Tm values.

The PSMA-BiTE1 formulations in phosphate buffer at pH 5.5-6.5 and in citrate buffer at pH 5.0-6.5 exhibited the highest melting points (Tm>63.0° C. according to the DSF method).

Example 2

The Influence of Non-Ionic Surfactants on PSMA-BiTE1 Aggregate Formation

The PSMA-BiTE1 molecules formed aggregates following the agitation stress test in all buffer systems tested. The efficiency with which aggregated PSMA-BiTE1 molecules bring about T-cell activation is not predictable or controllable, or only predictable or controllable to a limited extent. Therefore, it was imperative to find a stabilizer which prevents the aggregate formation resulting from agitation stress or the action of shear forces. In the agitation stress test, it became apparent that various non-ionic surfactants (e.g. polysorbate 80 or 20) stabilize the PSMA-BiTE1 molecules and can prevent aggregation. Surfactant concentrations between 0.01 and 0.04% (mass/volume) were sufficient for stabilization (see tables 3-7).

Example 3

PSMA-BiTE1 Dimer Formation in the Presence of Polyvalent Cations

A rise in the proportion of PSMA-BiTE1 aggregates during the concentration of PSMA-BiTE1 formulations could not be prevented by adding non-ionic surfactants.

Therefore, the electrostatic stabilization of the PSMA-BiTE1 molecules in the presence of polyvalent cations (e.g. $Mg^{2+}$ and $Ca^{2+}$) was examined. Polyvalent ions have a direct influence on the surface potential of dissolved proteins and can thus act in a stabilizing or even destabilizing manner.

The PSMA-BiTE1 molecules can be stabilized using magnesium chloride. The proportion of PSMA-BiTE1 dimers rose only negligibly following concentration and remained below <3% (table 3). The proportions of monomers and dimers were measured via size-exclusion chromatography (SEC).

TABLE 3

PSMA-BiTE1 molecules after concentration (in 50 mM Na$_2$HPO$_4$ and 50 mM lysine, pH 7.3)

| Additives during concentration | Protein content [mg/ml] | Monomers [%] | Dimers [%] |
|---|---|---|---|
| — | 2.04 | 95.7 | 4.3 |
| 0.04% (mass/volume) polysorbate 20 | 2.09 | 91.2 | 8.8 |
| 100 mM MgCl$_2$ | 2.13 | 98.1 | 1.9 |

SEC = size-exclusion chromatography

However, the addition of inorganic salts in higher concentrations is not pharmaceutically safe, and/or said additives represent a challenge in freeze-drying. For this reason, a search was carried out for alternative excipients which stabilize the PSMA-BiTE1 molecules and are, at the same time, pharmaceutically safe.

Example 4

Identification of Alternative Excipients for Stabilizing the PSMA-BiTE1 Monomers By chance, various amino acids and the derivatives thereof were, inter alia, included in the tests on stabilizing the PSMA-BiTE1 monomers in higher concentrations Amino acids and the derivatives thereof are not inorganic salts and are therefore classified as pharmaceutically safe. Some of these substances (e.g. lysine) exhibited, surprisingly, a positive influence on the stability of the PSMA-BiTE1 molecules during and after concentration (table 4).

The PSMA-BiTE1 stability in the phosphate buffer at pH 6.0 was astonishing. It was possible to suddenly concentrate the molecules to 1.6 mg/ml in a formulation comprising 50 mM $Na_2HPO_4$, 50 mM lysine, 0.04% polysorbate 20 and 10% trehalose dihydrate at pH 6.0, without aggregation occurring as a result of the action of agitation stress.

TABLE 4

PSMA-BiTE1 molecules after concentration at pH 7.3

| Buffer | Protein content [mg/ml] | SEC Monomers [%] | SEC Dimers [%] | DLS Median [nm] | State after agitation stress |
|---|---|---|---|---|---|
| 50 mM $Na_2HPO_4$ + 50 mM lysine 0.02% (mass/volume) polysorbate 20, 10% trehalose dihydrate | 1.94 | 95.1 | 4.9 | 11 | Turbid |
| 50 mM $Na_2HPO_4$ + 100 mM lysine 0.04% (mass/volume) polysorbate 20, 10% trehalose dihydrate | 1.88 | 97.5 | 2.5 | 9 | Turbid |
| 10 mM $Na_2HPO_4$ + 50 mM lysine + 100 mM histidine 0.04% (mass/volume) polysorbate 20, 10% trehalose dihydrate | 2.15 | 92.4 | 7.6 | 10 | OK |

SEC = size-exclusion chromatography;
DLS = dynamic light scattering; a turbid solution following agitation stress indicates a high proportion of BiTE aggregates, a clear or minimally clouded solution (state "OK") indicates a negligible degree of aggregation.

By adding lysine and histidine in a phosphate buffer, the PSMA-BiTE1 molecules could be concentrated without the formation of unacceptable proportions of dimers (≥5%). However, the formulations in which the proportion of dimers was low (<5%) destabilized during the agitation stress test, and this was recognizable from the clouding of the solution (test volumes 1 and 2; "Turbid" indicates aggregation, "OK" indicates little or no aggregation).

Example 5

Influence of pH on the Stability of the PSMA-BiTE1 Molecules

To examine the influence of pH on dimer formation, a formulation having pH 6.0 was produced. It exhibited a proportion of dimers which was comparable to those of the formulations at pH 7.3. Furthermore, the proportion of dimers was also stable during agitation stress, and this was apparent from the lack of clouding (table 5). The positive influence of pH 6.0 was used for the additional search for suitable stabilizers and formulations.

Example 6

Examination of Buffer Combinations

In a further experiment, a possible synergistic effect with regard to an increase in the stability of the PSMA-BiTE1 molecules by additives such as arginine, TEA or TRIS in combination with phosphate was examined. The lowest proportion of PSMA-BiTE1 dimers of 0.8% occurred in the case of the buffer combination 50 mM $Na_2HPO_4$, 100 mM TRIS at pH 6.0. The formulation was also sufficiently stable after agitation stress, and this was recognizable from the absent clouding of the solution (table 6). The stabilizing effect of TRIS was surprising, since the addition of arginine or TEA, which are both known for their stabilizing (i.e. aggregation-reducing) effect in the case of proteins, had no stabilizing effect in the case of the PSMA-BiTE molecules.

TABLE 5

PSMA-BiTE1 molecules after concentration at pH 6.0

| Buffer at pH 6.0 | Protein content [mg/ml] | SEC Monomers [%] | SEC Dimers [%] | DLS Median [nm] | State after agitation stress |
|---|---|---|---|---|---|
| 50 mM $Na_2HPO_4$ + 50 mM lysine 0.04% (mass/volume) polysorbate 20, 10% (mass/volume) trehalose dihydrate | 1.62 | 95.7 | 4.3 | 8 | OK |

SEC = size-exclusion chromatography;
DLS = dynamic light scattering

TABLE 6

PSMA-BiTE1 molecules after concentration with various additives at pH 6.0

| Buffer at pH 6.0 | Protein content [mg/ml] | SEC Monomers [%] | SEC Dimers [%] | DLS Median [nm] | State after agitation stress |
|---|---|---|---|---|---|
| 50 mM Na$_2$HPO$_4$ 0.04% (mass/volume) polysorbate 80, 4% (mass/volume) trehalose dihydrate | 1.82 | 96.4 | 3.3 | 13 | OK |
| 50 mM Na$_2$HPO$_4$ + 100 mM TRIS 0.04% (mass/volume) polysorbate 80, 4% (mass/volume) trehalose dihydrate | 1.81 | 99.2 | 0.8 | 12 | OK |
| 50 mM Na$_2$HPO$_4$ + 100 mM arginine 0.04% (mass/volume) polysorbate 80, 4% (mass/volume) trehalose dihydrate | 2.20 | 96.2 | 3.5 | 15 | OK |
| 50 mM Na$_2$HPO$_4$ + 100 mM TEA 0.04% (mass/volume) polysorbate 80, 4% (mass/volume) trehalose dihydrate | 1.88 | 96.2 | 3.4 | 11 | OK |

SEC = size-exclusion chromatography;
DLS = dynamic light scattering

As shown in example 1, the use of citrate buffer led to an increase in the thermal stability of PSMA-BiTE1 molecules. However, after concentration of the test volumes, the proportion of dimers in the citrate-buffered test volumes was substantially higher than in those with phosphate buffer (table 7 compared with table 6). Phosphate buffer is consequently better suited than citrate buffer for minimizing the formation of PSMA-BiTE1 dimers during concentration. Also, citrate in a formulation can lead to glass delamination and should no longer be used.

TABLE 7

PSMA-BiTE1 molecules after concentration at pH 6.0

| Buffer | Protein content [mg/ml] | SEC Monomers [%] | SEC Dimers [%] | DLS Median [nm] | State after agitation stress |
|---|---|---|---|---|---|
| 50 mM citrate 0.04% (mass/volume) polysorbate 80, 4% (mass/volume) trehalose dihydrate | 1.90 | 93.4 | 6.4 | 11 | OK |
| 50 mM citrate + 100 mM TRIS 0.04% (mass/volume) polysorbate 80, 4% (mass/volume) trehalose dihydrate | 1.95 | 92.9 | 7.0 | 12 | OK |

SEC = size-exclusion chromatography;
DLS = dynamic light scattering

Example 7

Thermal Stability of the PSMA-BiTE1 Molecules in TRIS-Phosphate Buffer Systems

The mean melting point ($T_{m1}$) of the PSMA-BiTE1 protein domain with the lowest molecular weight of the following formulation was determined:

0.2 mg/ml PSMA BiTE in 50 mM Na$_2$HPO$_4$, 100 mM TRIS, 0.04% polysorbate 80, 4% trehalose dihydrate, pH 6.0 (adjusted with HCl). By means of DSC, a $T_{m1}$ of 61.1° C. was measured.

Example 8

Influence of Agitation Stress on PSMA-BiTE1 Molecules in Phosphate/TRIS Formulations In general, BiTE molecules are physically destabilized by agitation stress, i.e. they form aggregates, which can be detected via Dynamic Light Scattering (DLS). The formation of aggregates even takes place at low BiTE concentrations of about 0.2 mg/ml. By contrast, in the case of a protein content of below 0.2 mg/ml, the BiTE molecules increasingly adsorb to the vessel wall.

By adding a surfactant (e.g. polysorbate 20 or 80), it was possible to prevent the adsorption of the PSMA-BiTE1 molecules to the vessel wall (e.g. of injection syringes, infusion bags, etc.) in some buffer systems (e.g. in phosphate- and lysine-based buffers), and similarly the formation of aggregates in the resting state. Polysorbate 80 must be present in a concentration of at least 0.002% in the composition in order to prevent the adsorption of the PSMA-BiTE1 molecules.

By dissolving the PSMA-BiTE1 molecules in a phosphate buffer with surfactant additive at pH 6.0, it was possible to prevent the formation of aggregates both in the resting state and during the action of agitation stress. The aforementioned formulation (phosphate buffer with surfactant additive at pH 6.0) was superior to the formulations with lysine with respect to minimizing the formation of aggregates.

TABLE 8

Formation of PSMA-BiTE1 aggregates following agitation stress; all samples contain 0.2 mg/ml PSMA-BiTE1 molecules and 0.02% (mass/volume) polysorbate 80

|  | pH | Visually | Content [%] | DLS D50% [nm] |
|---|---|---|---|---|
| $Na_2HPO_4$ | 6.0 | OK | 103.2 | 9 |
|  | 6.5 | OK | 78.6 | 2451* |
|  | 7.0 | OK | 52.9 | 1114* |
|  | 7.5 | OK | 66.5 | 8 |
| Lysine | 6.5 | OK | 68.5 | 2945* |
| $Na_2HPO_4$-lysine-histidine | 6.5 | OK | 119.5 | 11 |
| $Na_2HPO_4$-TRIS** | 6.0 | OK | 99.0 | 6 |

*Aggregates
**Monomers 99.6%; dimers 0.4%

Example 9

Dependence of PSMA-BiTE1 Aggregation on Concentration

In standard buffer systems, the proportion of dimers and multimers increased with the concentration of PSMA-BiTE1 molecules. However, dimers and multimers are acceptable to only a limited extent in formulations for therapeutic use, since they can influence the effectiveness of the formulation and of the therapeutic protein and provoke undesired immunological effects. Typically, the dimers are limited to a value of max. 5% and attempts are made to keep below said value as far as possible. Multimers and low-molecular-weight (LMW) fragments ought to be minimized as well, or not present at all. The monomer/dimer ratio, as well as the proportion of multimers and low-molecular-weight fragments, is measured using size-exclusion chromatography (SEC).

Using the buffer system comprising 50 mM $Na_2HPO_4$ and 100 mM TRIS at pH 6.0, it was possible to sufficiently reduce the formation of dimers and multimers amongst the PSMA-BiTE1 molecules during concentration.

This buffer system made it possible to produce a stable BiTE formulation having a content of >2 mg/ml (table 9).

TABLE 9

PSMA-BiTE1 molecules in 50 mM $Na_2HPO_4$ and 100 mM TRIS at pH 6.0

| Protein content [mg/ml] | 0.321 | 0.333 | 0.530 | 0.883 | 1.308 | 1.330 | 2.138 | 3.228 |
|---|---|---|---|---|---|---|---|---|
| Monomers [%] | 98.17 | 98.30 | 97.89 | 95.15 | 98.33 | 95.95 | 96.28 | 96.97 |
| Dimers [%] | 0.58 | 0.42 | 1.18 | 1.71 | 1.14 | 1.92 | 2.26 | 2.03 |
| Multimers [%] | <0.05 | <0.05 | <0.05 | <0.05 | <0.05 | <0.05 | <0.05 | <0.05 |
| LMW [%] | 1.24 | 1.28 | 0.93 | 3.14 | 0.53 | 2.14 | 1.45 | 1.00 |

LMW = low-molecular-weight fragments

Example 10

Influence of Trehalose and Polysorbate on PSMA-BiTE1 Stability

The addition of trehalose and polysorbate does not lead to increased formation of dimers, multimers, or LMW fragments, as can be determined by means of SEC measurement.

Example 10a

Influence of Trehalose and Polysorbate on PSMA-BiTE1 Stability

The addition of trehalose dihydrate and polysorbate did not lead to increased formation of dimers, multimers, or LMW fragments (table 10).

TABLE 10

PSMA-BiTE1 molecules in 50 mM $Na_2HPO_4$ and 100 mM TRIS at pH 6.0 with/without trehalose and polysorbate 80

| Polysorbate 80 (% mass/volume) | — | 0.04% | — | 0.04% |
|---|---|---|---|---|
| Trehalose dihydrate (% mass/volume) | — | — | 4% | 4% |
| Protein content [mg/ml] | 1.209 | 1.235 | 1.191 | 1.217 |
| SEC Monomers [%] | 98.3 | 98.3 | 98.5 | 98.2 |
| Dimers [%] | 1.6 | 1.7 | 1.5 | 1.7 |
| Multimers [%] | 0.1 | 0.1 | <0.05 | 0.1 |
| LMW [%] | <0.05 | <0.05 | <0.05 | <0.05 |

Example 11

Storage Stability of the PSMA-BiTE1 Molecules

The storage stability of the PSMA-BiTE1 molecules can be determined on the basis of the increase in the proportion of dimers and/or multimers as a function of the storage time.

The more rapid the increase in the proportion of these aggregates, the lower the storage stability.

It can be shown experimentally that the PSMA-BiTE1 molecules in a concentration of 90 µg/ml, 500 µg/ml and 2 mg/ml are stable for a period of 9 days with respect to formation of dimers and/or multimers. The formulations are kept in injection syringes at about 2-8° C., following an initial phase of from 4 to 16 hours at room temperature (about 20° C.). The compositions contain, in addition to the PSMA-BiTE1 molecules, 50 mM $Na_2HPO_4$, 100 mM TRIS, 0.04% polysorbate 80 and 4% trehalose. The proportion of PSMA-BiTE1 monomers is measured using SEC-HPLC and compared with the proportion of PSMA-BiTE1 monomers at the start of the experiments (i.e. on day 0).

Example 11a

Storage Stability of the PSMA-BiTE1 Molecules

The storage stability of the PSMA-BiTE1 molecules can be determined on the basis of the increase in the proportion of dimers and/or multimers as a function of the storage time. The more rapid the increase in the proportion of these aggregates, the lower the storage stability.

It was possible to show experimentally that the PSMA-BiTE1 molecules in a concentration of 90 µg/ml, 500 µg/ml and 2 mg/ml were stable for a period of 9 days with respect to formation of dimers and/or multimers (table 11). The formulations were kept in injection syringes at about 2-8° C., following an initial phase of from 4 to 16 hours at room temperature (about 20° C.). The compositions contained, in addition to the PSMA-BiTE1 molecules, 50 mM $Na_2HPO_4$, 100 mM TRIS, 0.04% polysorbate 80 and 4% trehalose dihydrate. The proportion of PSMA-BiTE1 monomers was measured using SEC-HPLC and compared with the proportion of PSMA-BiTE1 monomers at the start of the experiments (i.e. on day 0). After 9 days in the case of compositions having a PSMA-BiTE1 starting concentration of 90 µg/ml and 500 µg/ml, this relative purity was 100%, i.e. the proportion of the monomers had not lowered over this time. In the case of the compositions having 2 mg/ml PSMA-BiTE1 molecules, the relative purity was 97% after 9 days, absolutely corresponding to a decrease in the monomers by about 3% (from 97.58% on day 0 to 94.81% on day 9).

In other experiments, in the liquid formulation having a PSMA-BiTE1 concentration of 2 mg/ml at 2-8° C. over the course of a week, there was a moderate rise in the proportion of dimers by 2.5% (from 3% to 5.5%), coupled with a stable proportion of multimers (table 12). At this concentration, the PSMA-BiTE1 molecules are thus stable for a sufficiently long time to ensure container filling with virtually no losses and usage with virtually no losses.

For long-term storage (i.e. storage for a period considerably longer than one week), PSMA-BiTE1 solutions can, however, be either frozen (−80° C.) or lyophilized to ensure their stability. Lyophilization of the PSMA-BITE1-containing formulations with preservation of bioactivity was possible, as shown in example 17.

TABLE 12

Storage stability of the BiTE formulation at 2-8° C. (PSMA-BiTE1 concentration 2 mg/ml)

| Storage time [days] | SEC Monomers [%] | SEC Dimers [%] | SEC Multimers [%] |
|---|---|---|---|
| Start | 96.4 | 3.0 | 0.6 |
| 0.25 | 96.2 | 3.2 | 0.6 |
| 0.5 | 96.0 | 3.4 | 0.6 |
| 0.75 | 95.9 | 3.6 | 0.5 |
| 1 | 95.8 | 3.7 | 0.5 |
| 3 | 95.7 | 4.0 | 0.4 |
| 7 | 94.2 | 5.5 | 0.4 |
| 15 | 93.7 | 6.1 | 0.2 |
| 28 | 92.6 | 7.2 | 0.2 |
| 65 | 90.7 | 9.2 | 0.2 |
| 94 | 90.3 | 9.5 | 0.2 |
| 161 | 88.2 | 11.3 | 0.5 |
| 251 | 87.8 | 11.7 | 0.5 |

Example 12

Influence of pH on PSMA-BiTE1 Stability

In principle, PSMA-BiTE1 molecules are stable in the selected formulation containing TRIS, phosphate (in this case: $Na_2HPO_4$), trehalose and polysorbate within a pH range between pH 5.0 and 7.5. However, at a pH above pH 6, the proportion of dimers increases following shear stress.

TABLE 11

Determination of the purity (i.e. the proportion of monomers) of the PSMA-BiTE molecules by means of SEC-HPLC over a period of 9 days

| Day | PSMA-BiTE1 concentration [µg/ml] | Purity, proportion of monomers [%] | | | | Standard deviation | CV [%] | Relative purity (proportion of monomers) compared to T0 value | | | |
|---|---|---|---|---|---|---|---|---|---|---|---|
| | | Test 1 | Test 2 | Test 3 | Mean | | | Test 1 | Test 2 | Test 3 | Mean |
| 0 | 90 | 98.30 | 98.21 | 98.20 | 98.24 | 0.06 | 0.1 | — | — | — | — |
| 2 | | 98.35 | 98.39 | 98.37 | 98.37 | 0.02 | 0.0 | 100 | 100 | 100 | 100 |
| 7 | | 98.59 | 98.53 | 98.40 | 98.51 | 0.10 | 0.1 | 100 | 100 | 100 | 100 |
| 9 | | 98.37 | 98.36 | 98.39 | 98.37 | 0.02 | 0.0 | 100 | 100 | 100 | 100 |
| 0 | 500 | 97.93 | 97.95 | 98.01 | 97.96 | 0.04 | 0.0 | — | — | — | — |
| 2 | | 98.03 | 98.07 | 97.77 | 97.96 | 0.16 | 0.2 | 100 | 100 | 100 | 100 |
| 7 | | 97.90 | 97.67 | 97.91 | 97.83 | 0.14 | 0.1 | 100 | 100 | 100 | 100 |
| 9 | | 97.71 | 97.66 | 97.87 | 97.75 | 0.11 | 0.1 | 100 | 100 | 100 | 100 |
| 0 | 2000 | 97.45 | 97.54 | 97.75 | 97.58 | 0.15 | 0.2 | — | — | — | — |
| 2 | | 96.61 | 96.69 | 96.57 | 96.62 | 0.06 | 0.1 | 99 | 99 | 99 | 99 |
| 7 | | 94.79 | 95.34 | 95.04 | 95.06 | 0.28 | 0.3 | 97 | 98 | 97 | 97 |
| 9 | | 94.71 | 94.88 | 94.84 | 94.81 | 0.09 | 0.1 | 97 | 97 | 97 | 97 |

Example 12a

Influence of pH on PSMA-BiTE1 Stability

In principle, PSMA-BiTE1 molecules are stable in the selected formulation containing TRIS, phosphate (in this case: $Na_2HPO_4$), trehalose dihydrate and polysorbate within a pH range between pH 5.0 and 7.5. However, at a pH above pH 6, the proportion of dimers (>2%) increases following shear stress (table 13).

TABLE 13

2 mg PSMA-BiTE1 molecules per ml in 50 mM $Na_2HPO_4$, 100 mM TRIS, pH [variable]; 4% (mass/volume) trehalose dihydrate, 0.04% (% mass/volume) polysorbate 80

| pH | 5.0 | 5.5 | 6.0 | 6.5 | 7.0 | 7.5 |
|---|---|---|---|---|---|---|
| After production | | | | | | |
| Protein content [mg/ml] | 2.01 | 2.02 | 2.11 | 1.90 | 2.13 | 2.20 |
| DLS (D50%) [nm] | 10 | 11 | 15 | 11 | 12 | 10 |
| SEC Monomers [%] | 98.62 | 97.88 | 98.48 | 97.74 | 98.58 | 98.53 |
| Dimers [%] | 1.22 | 1.81 | 1.36 | 1.96 | 1.42 | 1.47 |
| Multimers [%] | <0.05 | <0.05 | <0.05 | <0.05 | <0.05 | <0.05 |
| LMW [%] | 0.15 | 0.31 | 0.16 | 0.30 | <0.05 | <0.05 |
| After shear stress | | | | | | |
| Protein content [mg/ml] | 2.00 | 2.01 | 2.11 | 1.90 | 2.13 | 2.20 |
| Protein content [%] | 99.5 | 99.6 | 99.8 | 100.1 | 99.9 | 100.1 |
| DLS (D50%) [nm] | 10 | 15 | 12 | 10 | — | — |
| SEC Monomers [%] | 98.37 | 98.21 | 98.23 | 97.83 | 97.42 | 97.53 |
| Dimers [%] | 1.63 | 1.79 | 1.77 | 2.17 | 2.58 | 2.47 |
| Multimers [%] | <0.05 | <0.05 | <0.05 | <0.05 | <0.05 | <0.05 |
| LMW [%] | <0.05 | <0.05 | <0.05 | <0.05 | <0.05 | <0.05 |

Example 13

Influence of TRIS and Phosphate on PSMA-BiTE1 Stability

Investigations with respect to different buffer strengths in the formulation showed that the buffer strengths in the formulation can be varied: from 20 to 100 mM $Na_2HPO_4$ and from 50 to 200 mM TRIS at pH 6.0 are useful with respect to minimizing the formation of PSMA-BiTE1 dimers. All combinations allow concentration and the action of shear stress.

In the absence of TRIS, it was not possible to concentrate the PSMA-BiTE1 molecules, and in the absence of $Na_2HPO_4$, the proportion of dimers rose to over >2% following the action of shear stress. Also, the phosphate buffer exhibited good buffering action at pH 6.0 and supports the thermal stability of the PSMA-BiTE1 molecules.

TABLE 14

2 mg/ml PSMA-BiTE1 molecules in [variable] $Na_2HPO_4$, [variable] TRIS, pH 6.0, 4% (mass/volume) trehalose dihydrate, 0.04% (mass/volume) polysorbate 80

| | $Na_2HPO_4$ [mM] | | | | | |
|---|---|---|---|---|---|---|
| | — | 20 | 50 | 50 | 50 | 100 |
| | TRIS [mM] | | | | | |
| | 100 | 100 | 100 | 50 | 200 | 100 |
| After production | | | | | | |
| Protein content [mg/ml] | 2.23 | 2.08 | 2.11 | 2.19 | 2.17 | 2.07 |
| DLS (D50%) [nm] | 11 | 9 | 15 | 12 | 15 | 12 |
| SEC Monomers [%] | 98.11 | 98.78 | 98.48 | 99.22 | 99.01 | 99.19 |
| Dimers [%] | 1.57 | 1.22 | 1.36 | 0.78 | 0.99 | 0.81 |
| Multimers [%] | <0.05 | <0.05 | <0.05 | <0.05 | <0.05 | <0.05 |
| LMW [%] | 0.31 | <0.05 | 0.16 | <0.05 | <0.05 | 0.30 |
| After shear stress | | | | | | |
| Protein content [mg/ml] | 2.22 | 2.08 | 2.11 | 2.20 | 2.16 | 2.08 |
| Protein content [%] | 99.9 | 100.0 | 99.8 | 100.4 | 99.9 | 100.1 |
| DLS (D50%) [nm] | — | — | 12 | 13 | 13 | 12 |
| SEC Monomers [%] | 97.90 | 98.26 | 98.23 | 98.55 | 98.32 | 98.60 |
| Dimers [%] | 2.10 | 1.73 | 1.77 | 1.45 | 1.68 | 1.40 |
| Multimers [%] | <0.05 | <0.05 | <0.05 | <0.05 | <0.05 | <0.05 |
| LMW [%] | <0.05 | <0.05 | <0.05 | <0.05 | <0.05 | <0.05 |

Example 14

Influence of Various Wetting Agents on PSMA-BiTE1 Stability

Various polysorbates can stabilize the PSMA-BiTE1 molecules in the formulation against shear stress. However, the best results were achieved with polysorbate 80. Other stabilizers such as, for example, Synperonic F68 likewise had positive effects.

From 0.04% to 0.10% (mass/volume) polysorbate 80 had a good stabilizing effect on the PSMA-BiTE1 molecules during the shear stress. 0.004% (mass/volume) polysorbate was not sufficient here to prevent an unacceptable increase in the formation of dimers following the action of shear stress.

TABLE 15

2 mg/ml PSMA-BiTE1 molecules in 50 mM $Na_2HPO_4$, 100 mM TRIS, pH 6.0, 4% (mass/volume) trehalose dihydrate, [variable] wetting agent

| | Wetting agent | | | | |
|---|---|---|---|---|---|
| | Polysorbate 80 | Polysorbate 20 | Synperonic F68 | Polysorbate 80 | Polysorbate 80 |
| Wetting agent [% (mass/volume)] | 0.04 | 0.04 | 0.04 | 0.004 | 0.10 |
| After production | | | | | |
| Protein content [mg/ml] | 2.11 | 2.13 | 2.10 | 2.13 | 2.08 |
| DLS (D50%) [nm] | 15 | 12 | 10 | 13 | 14 |

TABLE 15-continued 2 mg/ml PSMA-BiTE1 molecules in 50 mM Na$_2$HPO$_4$, 100 mM TRIS, pH 6.0, 4% (mass/volume) trehalose dihydrate, [variable] wetting agent

| | Wetting agent | | | | |
|---|---|---|---|---|---|
| | Polysorbate 80 | Polysorbate 20 | Synperonic F68 | Polysorbate 80 | Polysorbate 80 |
| SEC Monomers [%] | 98.48 | 97.92 | 98.59 | 98.47 | 98.36 |
| Dimers [%] | 1.36 | 2.08 | 1.24 | 1.36 | 1.46 |
| Multimers [%] | <0.05 | <0.05 | <0.05 | <0.05 | <0.05 |
| LMW [%] | 0.16 | <0.05 | 0.16 | 0.17 | 0.17 |
| After shear stress | | | | | |
| Protein content [mg/ml] | 2.11 | 2.11 | 2.10 | 1.98 | 2.07 |
| Protein content [%] | 99.8 | 99.2 | 99.9 | 93.3 | 99.5 |
| DLS (D50%) [nm] | 12 | 14 | 10 | 3139 | 15 |
| SEC Monomers [%] | 98.23 | 96.54 | — | 92.54 | 98.09 |
| Dimers [%] | 1.77 | 3.46 | — | 7.46 | 1.91 |
| Multimers [%] | <0.05 | <0.05 | — | <0.05 | <0.05 |
| LMW [%] | <0.05 | <0.05 | — | <0.05 | <0.05 |

Example 15

Influence of the PSMA-BiTE1 Concentration on the Stability of the Formulation

Using the formulation 50 mM Na$_2$HPO$_4$, 100 mM TRIS, pH 6.0, 4% (mass/volume) trehalose, 0.04% (mass/volume) polysorbate 80, it is possible to produce PSMA-BiTE1 concentrations up to 2 mg/ml. At higher PSMA-BiTE1 concentrations, the proportion of dimers distinctly increases. However, unacceptable values are measured only at PSMA-BiTE concentrations of greater than 4 mg/ml and after the action of shear forces (9.25% dimers at a PSMA-BiTE concentration of about 11.2 mg/ml).

Example 15a

Influence of the PSMA-BiTE1 Concentration on the Stability of the Formulation

Using the formulation 50 mM Na$_2$HPO$_4$, 100 mM TRIS, pH 6.0, 4% (mass/volume) trehalose dihydrate, 0.04% (mass/volume) polysorbate 80, it was possible to produce PSMA-BiTE1 concentrations up to 2 mg/ml. At higher PSMA-BiTE1 concentrations, the proportion of dimers distinctly increased. However, unacceptable values were measured only at PSMA-BiTE concentrations of greater than 4 mg/ml and after the action of shear forces (9.25% dimers at a PSMA-BiTE concentration of about 11.2 mg/ml).

TABLE 16

[Variable] mg/ml PSMA-BiTE1 molecules in 50 mM Na$_2$HPO$_4$, 100 mM TRIS, pH 6.0, 4% (mass/volume) trehalose dihydrate, 0.04% (mass/volume) polysorbate 80

| | PSMA-BiTE1 conc. [mg/ml] | | | |
|---|---|---|---|---|
| | 0.4 | 2 | 4 | 11 |
| After production | | | | |
| Protein content [mg/ml] | 0.44 | 2.11 | 4.42 | 11.17 |
| DLS (D50%) [nm] | 12 | 15 | 17 | 18 |
| SEC Monomers [%] | 98.67 | 98.48 | 96.62 | 95.63 |
| Dimers [%] | 1.16 | 1.36 | 2.82 | 3.73 |
| Multimers [%] | <0.05 | <0.05 | <0.05 | <0.05 |
| LMW [%] | 0.16 | 0.16 | 0.56 | 0.63 |
| After shear stress | | | | |
| Protein content [mg/ml] | 0.44 | 2.11 | 4.39 | 11.32 |
| Protein content [%] | 99.8 | 99.8 | 99.2 | 101.3 |
| DLS (D50%) [nm] | 10 | 12 | 12 | 16 |
| SEC Monomers [%] | 99.53 | 98.23 | 96.32 | 90.75 |
| Dimers [%] | 0.47 | 1.77 | 3.68 | 9.25 |
| Multimers [%] | <0.05 | <0.05 | <0.05 | <0.05 |
| LMW [%] | <0.05 | <0.05 | <0.05 | <0.05 |

Example 16

Lyophilization

After finishing the PSMA-BiTE1 composition, it was lyophilized. Numerous freeze-drying units are available for this purpose, for example the Genesis Super XL from SP Scientific. Freeze-drying is achieved by the freezing of a substance and the subsequent sublimation of the ice without passing through a liquid phase.

TABLE 17

Program for freeze-drying PSMA-BiTE formulations (total time: 42 h).

| | Ts [° C.] | t [min] | Vacuum [μbar] | Ramp/hold |
|---|---|---|---|---|
| Freezing phase | | | | |
| 1 | Room temperature | 0 | — | Hold |
| 2 | −45 | 30 | — | Ramp |
| 3 | −45 | 240 | — | Hold |
| Primary drying | | | | |
| 1 | −20 | 60 | 100 | Ramp |
| 2 | −20 | 1000 | 100 | Hold |

TABLE 17-continued

Program for freeze-drying PSMA-BiTE formulations (total time: 42 h).

|  | Ts [° C.] | t [min] | Vacuum [µbar] | Ramp/ hold |
|---|---|---|---|---|
| Secondary drying |  |  |  |  |
| 1 | 25 | 60 | 10 | Ramp |
| 2 | 25 | 1140 | 10 | Hold |

"Ramp" = continuous temperature increase or decrease

In the freezing phase, the product was cooled down in a "ramp", i.e. continuously, within 30 min from room temperature to −45° C. To completely freeze the product solution, this temperature was held for 240 min.

This was followed by the primary drying phase. At a chamber vacuum of 100 Oar, the composition was heated within 60 min to −20° C. This temperature is held for 1000 min; the primary drying was then completed. For the subsequent secondary drying, the composition was heated in a vacuum of 10 µbar to 25° C. These conditions were held for 1140 min in order to remove the residual water down to ≤2% (detection by means of Karl Fischer titration).

At the end of the drying process, the unit was vented and the lyophilization vessels sealed.

Example 17a

Bioactivity of PSMA-BiTE1 Lyophilisates after Long-Term Storage and Reconstitution Compositions containing PSMA-BiTE1 molecules (table 18a) were stored as lyophilisate for up to 12 months at 2-8° C. and at 25° C./60% relative humidity. After 3 and 12 months, solution was reconstituted from lyophilisate in each case and analysed in a cell-based activity assay. The measurements (by means of the CytoTox-Glo Cytotoxicity Assay from Promega) revealed unchanged bioactivity, after both 6- and 12-month storage under the aforementioned conditions.

Furthermore, the storage stability of the reconstituted PSMA-BiTE1 solution was analysed. After reconstitution, the solution was first stored for 7 days in a refrigerator (2-8° C.) and then for 16 hours at room temperature (+20±5° C.). Subsequently, the bioactivity of the PSMA-BiTE1 molecules was also ascertained here by means of a cell-based activity assay. It was 96% in reconstituted solution after the aforementioned further storage.

The bioactivity of the PSMA-BiTE1 molecules in the lyophilized formulation was consequently stable after storage over 6-12 months under the aforementioned storage conditions. The same applies to the solution reconstituted from this lyophilisate after storage for 7 days at 2-8° C. and for 16 hours at room temperature.

Example 17b

Stability of Two Representative Batches—in Terms of Monomers (SEC and CGE), Bioactivity (Cell-Based Activity Assay) and Particles (HIAC and MFI)—of PSMA-BiTE1 Lyophilisates after Long-Term Storage and Reconstitution Compositions containing PSMA-BiTE1 molecules (table 18a) were stored as lyophilisate for up to 12 months at 2-8° C. and at 25° C./60% relative humidity. After 3 and 12 months, solution was reconstituted from lyophilisate in each case and analysed in, inter alia, a cell-based activity assay. The measurements (by means of the CytoTox-Glo Cytotoxicity Assay from Promega) revealed unchanged activities, and also only slight changes in the proportion of monomers in SEC and CGE, after both 3- and 12-month storage under the aforementioned conditions (table 18b).

In addition, protein particles ranging in size from >2 to >25 µm were measured by means of micro-flow imaging (MFI) and HIAC (table 18c). The values remained stable within the limits of measurement accuracy for both batches during the storage time.

TABLE 18a

Composition of the freeze-dried product. Each colourless injection glass vial contains a lyophilisate in the following composition:

| Composition | Function | Amount in mg[a] | Amount in percent of the solution before freeze-drying |
|---|---|---|---|
| Active ingredient |  |  |  |
| PSMA-BITE1 | Active ingredient | 2.60 | 0.2 |
| Excipients |  |  |  |
| Na₂HPO₄*2H₂O | Buffer substance | 11.57 | 0.89 |
| TRIS | Buffer substance | 15.73 | 1.21 |
| Trehalose dihydrate | Cryoprotectant | 52.00 | 4 |
| Polysorbate 80 | Surfactant | 0.52 | 0.04 |
| 10% HCl | pH adjustment | qs | qs |

[a]The amounts include 0.3 ml overfill

The lyophilisate is to be reconstituted with 1.2 ml water for injection. The solution for administration then obtained has a concentration of 2 mg/ml. A vial contains, as a result of the overfill, 1.3 ml with 2.6 mg PSMA-BITE1.

TABLE 18b

Stabilities of two batches of the formulation according to the invention of PSMA-BITE1

|  | SEC (monomers) | CGE (reduced) | CGE (not reduced) | Bioactivity |
|---|---|---|---|---|
| Batch 1 |  |  |  |  |
| Start | 97.3% | n.d. | n.d. | 101% |
| 3 months, 6° C. | n.d. | n.d. | n.d. | n.d. |
| 3 months, 25° C./60 | n.d. | n.d. | n.d. | n.d. |
| 12 months, 6° C. | 96.9% | 99.54% |  | 122.3% |
| 12 months, 25° C./60 | 95.8% | 99.51% | 100% | 100% |
| Batch 2 |  |  |  |  |
| Start | 98.0% |  |  | 92.8% |
| 3 months, 6° C. | 97.8% |  |  | 136% |
| 3 months, 25° C./60 | 97.7% |  |  | 131.2% |
| 12 months, 6° C. | 97% | 100 | 100 | 123.5% |
| 12 months, 25° C./60 | 96.71% | 100 | 100 | 112.7% |

TABLE 18c

Stabilities of two batches of the formulation according
to the invention of PSMA-BITE1 (protein particles)

| | HIAC | | | | MFI | | | |
|---|---|---|---|---|---|---|---|---|
| | 25 μm | 10 μm | 5 μm | 2 μm | 25 μm | 10 μm | 5 μm | 2 μm |
| Batch 1 | | | | | | | | |
| Start | 0 | 3 | 24 | 552 | 4 | 61 | 823 | 7239 |
| 3 months, 6° C. | 0 | 3 | 30 | 613 | 6 | 82 | 490 | 6697 |
| 3 months, 25° C./60 | 0 | 9 | 45 | 614 | 1 | 18 | 257 | 4663 |
| 12 months, 6° C. | 1 | 3 | 22 | 365 | 4 | 27 | 251 | 4788 |
| 12 months, 25° C./60 | 2 | 113 | 540 | 2296 | 18 | 317 | 1109 | 7557 |
| Batch 2 | | | | | | | | |
| Start | 0 | 3 | 40 | 808 | 2 | 39 | 404 | 6248 |
| 3 months, 6° C. | 0 | 2 | 22 | 483 | 3 | 23 | 287 | 5723 |
| 3 months, 25° C./60 | 0 | 2 | 25 | 565 | 2 | 19 | 346 | 6247 |
| 12 months, 6° C. | 1 | 4 | 94 | 777 | 2 | 11 | 148 | 3957 |
| 12 months, 25° C./60 | 0 | 3 | 56 | 769 | 2 | 8 | 253 | 6469 |

Furthermore, the storage stability of the reconstituted PSMA-BiTE1 solution was analysed. After reconstitution, the solution was first stored for 7 days in a refrigerator (2-8° C.) and then for 16 hours at room temperature (+20±5° C.). Subsequently, the bioactivity of the PSMA-BiTE1 molecules was also ascertained here by means of a cell-based activity assay. It was 96% in reconstituted solution after the aforementioned further storage.

After storage over 3 to 12 months under the aforementioned storage conditions, the bioactivity of the PSMA-BiTE1 molecules in the lyophilized formulation was consequently stable within the limits of measurement accuracy in each case. The other measurement parameters (SEC, bioactivity, MFI and HIAC data) also show this result. The same applies to the solution reconstituted from this lyophilisate after storage for 7 days at 2-8° C. and for 16 hours at room temperature.

Example 18

Influence of Shear Stress in Administration by
Means of Injection Syringe and Cannula on the
Formation of PSMA-BiTE1 Dimers Composition: 2.17 mg/ml PSMA-BiTE1 molecules, 50 mM $Na_2HPO_4$, 100 mM TRIS, pH 6.0, 4% trehalose, 0.04% polysorbate 80

Material:
Disposable syringes (BD 2 ml), cannulae (BD Microlance 30G1/2 (REF: 304000)) and brown-glass vials (6R) and CryoTubes.
Procedure:
30 vials are thawed. 6 vials are used as starting values. For each experiment, 6 vials are used, i.e. withdrawn using the syringe/cannula and all injected into a brown glass or CryoTube.
Experiments:
1. Slow injection of the PSMA-BiTE1 composition into a CryoTube (SyS Cryo)
2. Slow injection of the PSMA-BiTE1 composition into a brown glass (SyS Glass)
3. Rapid injection of the PSMA-BiTE1 composition into a CryoTube (SyR Cryo)
4. Rapid injection of the PSMA-BiTE1 composition into a brown glass (SyR Glass)

Subsequently, the formation of dimers is measured by means of differential scanning fluorimetry (DSF).

Example 18a

Influence of Shear Stress in Administration by
Means of Injection Syringe and Cannula on the
Formation of PSMA-BiTE1 Dimers Composition: 2.17 mg/ml PSMA-BiTE1 molecules, 50 mM $Na_2HPO_4$, 100 mM TRIS, pH 6.0, 4% trehalose dihydrate, 0.04% polysorbate 80
Material:
Disposable syringes (BD 2 ml), cannulae (BD Microlance 30G1/2 (REF: 304000)) and brown-glass vials (6R) and CryoTubes.
Procedure:
30 vials were thawed. 6 vials were used as starting values. For each experiment, 6 vials were used, i.e. withdrawn using the syringe/cannula and all injected into a brown glass or CryoTube.
Experiments:
1. Slow injection of the PSMA-BiTE1 composition into a CryoTube (SyS Cryo)
2. Slow injection of the PSMA-BiTE1 composition into a brown glass (SyS Glass)
3. Rapid injection of the PSMA-BiTE1 composition into a CryoTube (SyR Cryo)
4. Rapid injection of the PSMA-BiTE1 composition into a brown glass (SyR Glass)

TABLE 19

Formation of PSMA-BiTE1 dimers following action of
shear stress owing to injection

| | Start | SyS Cryo | SyS Glass | SyR Cryo | SyR Glass |
|---|---|---|---|---|---|
| PSMA-BiTE1 conc. [mg/ml] | 2.17 | 2.21 | 2.16 | 2.19 | 2.16 |
| SEC Monomers [%] | 96.6 | 96.5 | 96.4 | 96.4 | 96.4 |
| SEC Dimers [%] | 3.3 | 3.4 | 3.5 | 3.4 | 3.4 |
| SEC Multimers [%] | 0.1 | 0.1 | 0.1 | 0.1 | 0.1 |

The formation of dimers was measured by means of differential scanning fluorimetry (DSF). It was not possible to report a significant rise in the proportion of dimers after the injection of the composition by means of injection syringes and cannulae. This result shows that the formulation according to the invention is, in all cases, stable with respect to the action of generated shear forces.

Example 19

Stability of the PSMA-BiTE1 Solution after
Reconstitution (Up to 28 Hours at 2-8° C.) and at 2
Dilutions and 1 Temperature (25° C.) in 0.9%
Saline Solution for Up to 8 Hours The proportion of monomers, dimers and multimers was measured by means of SEC chromatography.
Composition: 2.0 mg/ml PSMA-BiTE1 molecules, 50 mM $Na_2HPO_4$, 100 mM TRIS, pH 6.0, 4% trehalose dihydrate, 0.04% polysorbate 80

Material:

0.9% NaCl and water for injection

Procedure:

16 lyophilized PSMA-BiTE1 vials were reconstituted by adding 1.1 ml water for injection (WFI). Of these vials, 8 vials were stored at 2-8° C., 4 vials were diluted with 0.9% NaCl solution to the concentration of 0.066 mg/ml, and 4 vials were diluted with 0.9% NaCl solution to the concentration of 0.66 mg/ml. They were incubated at 25° C. and examined at the times of 0 h, 2 h, 4 h and 8 h by means of SEC.

TABLE 20

PSMA-BiTE1 stability in the case of dilution in 0.9% NaCl solution and incubation at 25° C. for up to 8 hours, and also up to 28 hours at 2-8° C. in the case of the reconstituted solution.

| | | SEC | | |
|---|---|---|---|---|
| Sample description | [h] | Multi-mers | Dimers | Mono-mers |
| 2 mg/ml reconst. lyo, Start, RT | 0 | 0.3 | 2.0 | 97.7 |
| 2 mg/ml reconst. lyo, 1 h, 2-8° C. | 1 | 0.2 | 2.1 | 97.7 |
| 2 mg/ml reconst. lyo, 2 h, 2-8° C. | 2 | 0.2 | 2.1 | 97.7 |
| 2 mg/ml reconst. lyo, 4 h, 2-8° C. | 4 | 0.2 | 2.2 | 97.6 |
| 2 mg/ml reconst. lyo, 8 h, 2-8° C. | 8 | 0.3 | 2.3 | 97.5 |
| 2 mg/ml reconst. lyo, 12 h, 2-8° C. | 12 | 0.3 | 2.4 | 97.3 |
| 2 mg/ml reconst. lyo, 18 h, 2-8° C. | 18 | 0.2 | 2.5 | 97.2 |
| 2 mg/ml reconst. lyo, 28 h, 2-8° C. | 28 | 0.3 | 2.8 | 97.0 |
| 0.0666 mg/ml diluted in 0.9% NaCl, Start, RT | 0 | 0.1 | 1.9 | 98.0 |
| 0.0666 mg/ml diluted in 0.9% NaCl, 1 h, RT | 1 | 0.1 | 1.5 | 98.4 |
| 0.0666 mg/ml diluted in 0.9% NaCl, 4 h, RT | 4 | <0.05 | 1.2 | 98.7 |
| 0.0666 mg/ml diluted in 0.9% NaCl, 8 h, RT | 8 | <0.05 | 1.1 | 98.8 |
| 0.666 mg/ml diluted in 0.9% NaCl, Start, RT | 0 | 0.2 | 2.2 | 97.6 |
| 0.666 mg/ml diluted in 0.9% NaCl, 1 h, RT | 1 | 0.2 | 2.2 | 97.6 |
| 0.666 mg/ml diluted in 0.9% NaCl, 4 h, RT | 4 | 0.3 | 2.2 | 97.5 |
| 0.666 mg/ml diluted in 0.9% NaCl, 8 h, RT | 8 | 0.3 | 2.2 | 97.5 |

As expected, the samples reconstituted using WFI show again the increase in dimers which can be expected for a 2 mg/ml solution at 2-8° C. The decrease in monomers clearly correlates with the increase in dimers, and no multimers are formed.

The dilutions in 0.9% NaCl solution show a result comparable to the results in PBS. In the case of 0.666 mg/ml, the monomer/dimer ratio remains constant, and in the case of 0.066 mg/ml, there is in turn an increase in monomers.

Example 20

Model Experiment on the Stability of the PSMA-BITE1 Solution in the Case of Subcutaneous Administration To this end, the reconstituted PSMA-BiTE1 solution was examined in PBS at 2 dilutions and 2 temperatures (25° C. & 37° C.). Measurements were made of the proportion of monomers, dimers and multimers, and of fragments (LMW), by means of SEC chromatography, and also of sub-visible particles (SVP) by means of MFI.

Composition: 2.0 mg/ml PSMA-BiTE1 molecules, 50 mM $Na_2HPO_4$, 100 mM TRIS, pH 6.0, 4% trehalose dihydrate, 0.04% polysorbate 80

Material:

PBS

Procedure:

To determine the stability of the diluted PSMA-BITE-1 solutions under sc administration conditions, eight lyophilized PSMA-BiTE1 vials were each reconstituted by adding 1.1 ml WFI. Using PBS, 4 vials were diluted to the concentration of 0.066 mg/ml and 4 vials were diluted to the concentration of 0.66 mg/ml. They were incubated at 25° C. (control) and 37° C. and measured at the times of 0 h, 2 h, 4 h and 8 h by means of SEC and MFI.

TABLE 20

PSMA-BiTE1 stability in the case of dilution in PBS and incubation at 25° C. (top) and 37° C. (bottom) for up to 8 hours

| Sample | Dilution in PBS C [mg/ml] | Times [h] | SEC [%] | | | | MFI (particles/container) | | | |
|---|---|---|---|---|---|---|---|---|---|---|
| | | | Multimers | Dimers | Monomers | LMW | ≥2 μm | ≥5 μm | ≥10 μm | ≥25 μm |
| Dilution with PBS at 25° C. | | | | | | | | | | |
| 1 | 0.0666 | 0 | 0.05 | 1.92 | 98.03 | na | | | | |
| 2 | 0.0666 | 2 | 0.04 | 1.86 | 98.10 | na | | | | |
| 3 | 0.0666 | 4 | 0.05 | 1.85 | 98.10 | na | | | | |
| 4 | 0.0666 | 8 | 0.03 | 1.79 | 98.19 | na | 3336 | 2582 | 908 | 210 |
| 5 | 0.666 | 0 | 0.08 | 1.93 | 97.94 | 0.05 | | | | |
| 6 | 0.666 | 2 | 0.07 | 1.95 | 97.93 | 0.06 | | | | |
| 7 | 0.666 | 4 | 0.06 | 1.96 | 97.92 | 0.06 | | | | |
| 8 | 0.666 | 8 | 0.05 | 1.99 | 97.90 | 0.06 | 5729 | 876 | 246 | 39 |
| 9 | Only PBS | 0 | — | — | — | — | 1410 | 534 | 168 | 30 |
| Dilution with PBS at 37° C. | | | | | | | | | | |
| 1 | 0.0666 | 0 | 0.05 | 1.95 | 98.00 | na | | | | |
| 2 | 0.0666 | 2 | 0.02 | 1.58 | 98.40 | na | | | | |
| 3 | 0.0666 | 4 | na | 1.30 | 98.70 | na | | | | |
| 4 | 0.0666 | 8 | 0.02 | 0.97 | 99.02 | na | 726 | 198 | 82 | 24 |
| 5 | 0.666 | 0 | 0.10 | 1.96 | 97.88 | 0.06 | | | | |

TABLE 20-continued

PSMA-BiTE1 stability in the case of dilution in PBS and incubation at 25° C. (top) and 37° C. (bottom) for up to 8 hours

| Sample | Dilution in PBS C [mg/ml] | Times [h] | SEC [%] Multimers | Dimers | Monomers | LMW | MFI (particles/container) ≥2 µm | ≥5 µm | ≥10 µm | ≥25 µm |
|---|---|---|---|---|---|---|---|---|---|---|
| 6 | 0.666 | 2 | 0.05 | 1.92 | 97.97 | 0.06 | | | | |
| 7 | 0.666 | 4 | 0.05 | 1.89 | 97.99 | 0.07 | | | | |
| 8 | 0.666 | 8 | 0.05 | 1.88 | 98.00 | 0.07 | 5731 | 928 | 294 | 42 |

The dilution with PBS and incubation in PBS at 37° C. shows that the PSMA-BiTE1 molecule is stable under these simulated conditions of subcutaneous administration. In the case of 0.66 mg/ml, we have a stable monomer/dimer ratio for both incubation temperatures. By contrast, in the case of 0.066 mg/ml, we see the effect that the proportion of dimers decreases and the proportion of monomers increases. This is an effect of reversible dimer formation, which is concentration- and time-dependent. In the case of the SVPs, there is a tendency towards a slight concentration-, temperature- and time-dependent formation of SVPs, which, however, does not represent a stability problem. This shows the suitability of the formulation for subcutaneous administration.

Example 21

Stability of the PSMA-BiTE1 Dilutions in 0.9% NaCl Solutions for Dose-Range Finding Studies PSMA-BiTE1 lyophilisates were reconstituted with 1.2 ml WFI and admixed with 0.9% strength NaCl solution which was adjusted to a polysorbate 80 content of 0.004%. This was necessary in order to avoid losses in the bioactivity of the highly diluted solutions. To this end, a 1% strength polysorbate 80 solution in a 50 mM sodium phosphate buffer (pH 6.5) was produced. This solution was added to a commercially available 0.9% strength NaCl solution (e.g. Baxter Viaflo 250 ml) to achieve a final concentration of 0.004%. Using this solution, dilutions of PSMA-BiTE1 ranging from 0.05 µg/ml to 2000 µg/ml were produced in the following steps:
0.05 µg/ml
0.7 µg/ml
2 µg/ml
18 µg/ml
90 µg/ml
500 mg/ml
2000 µg/ml To this end, use was made of sterile, empty infusion bags (e.g. 150 ml bags from Impromediform GmbH, REF MF 1661)), into which the conditioned saline solution was initially charged. Corresponding amounts of reconstituted PSMA-BiTE1 solution were added to this solution and mixed by rotating the bag. 1 ml aliquots were filled into 2 ml syringes (e.g. Injekt 2 ml/Luer Lock Solo Braun (REF 46067001V)) and sealed with Combi stoppers from B. Braun (REF 4495101).

These syringes were then stored in a refrigerator at from 2 to 8° C. for up to 9 days. This storage included storage at RT (20° C.+/−5° C.) for 4 or 20 hours. For the measurement, an injection needle (BD Microlance 3 30G1/2" 0.3*13 mm) for subcutaneous administration was attached to the syringe (REF 304000) and the solution was expelled therethrough into a 2 ml vial (glass type 1).

The bioactivity of the diluted solutions was examined in a cytotoxicity assay. The recovery (protein content) was ascertained in an (electrochemiluminescent assay) ECL assay.

Owing to a limited measurement range in the ECL assay, it was necessary to dilute the assay solutions in the conditioned 0.9% strength saline solution prior to the analysis, as follows:
0.05 µg/ml: undiluted
0.7 µg/ml: 1:50
2 µg/ml: 1:200
18 µg/ml: 1:1000

Tables 21a and b show the results of the storage studies of the final injection solutions ranging from 0.05 to 18 µg/ml PSMA-BiTE1 over a storage time of 9 days. The protein concentration remains stable for all final concentrations. The relative concentrations (compared to the T0 values) are within the range from 79% to 117%. On the basis of previous experiences with this substance class, an acceptance criterion of from ±40% to ±50% difference in relation to the T0 value was ascertained. The measured data lie well within this acceptance range.

TABLE 21

Determination of the protein content by ECL assay within the range from 0.05 µg/ml to 18 µg/ml a

| Day | Nominal BiTE [µg/ml] | Concentration [µg/ml] A1 | A2 | A3 | A4 | Ave | STDEV | CV [%] | Recovery [%] | Rel. diff. to T0 value [%] |
|---|---|---|---|---|---|---|---|---|---|---|
| 0 | 0.05 | 0.049 | 0.058 | 0.044 | 0.044 | 0.049 | 0.01 | 13 | 98 | — |
| 2 | | 0.045 | 0.048 | 0.054 | 0.053 | 0.05 | 0 | 9 | 100 | 2 |
| 7 | | 0.041 | 0.047 | 0.049 | 0.045 | 0.046 | 0 | 8 | 91 | −7 |
| 9 | | 0.037 | 0.042 | 0.041 | 0.035 | 0.039 | 0 | 8 | 77 | −21 |
| 0 | 0.7 | 0.63 | 0.55 | 0.62 | 0.58 | 0.6 | 0.04 | 6 | 85 | — |
| 2 | | 0.43 | 0.63 | 0.81 | 0.81 | 0.67 | 0.18 | 27 | 96 | 12 |

TABLE 21-continued

Determination of the protein content by ECL assay within the range from 0.05 µg/ml to 18 µg/ml

| 7 |    | 0.51  | 0.52 | 0.49  | 0.65  | 0.54  | 0.07 | 13 | 77  | −9  |
|---|----|-------|------|-------|-------|-------|------|----|-----|-----|
| 9 |    | 0.67  | —    | 0.53  | 0.5   | 0.57  | 0.09 | 17 | 81  | −5  |
| 0 | 2  | 2.46  | 1.3  | 2.04  | 1.99  | 1.95  | 0.48 | 25 | 97  | —   |
| 2 |    | 1.32  | 1.62 | 2.21  | 2.17  | 1.83  | 0.44 | 24 | 91  | −6  |
| 7 |    | 1.14  | 1.74 | 1.46  | 2.02  | 1.59  | 0.38 | 24 | 79  | −18 |
| 9 |    | 2.62  | 2.02 | 1.75  | 1.85  | 2.06  | 0.39 | 19 | 103 | 6   |
| 0 | 18 | 11.37 | 9.44 | 11.74 | 9.6   | 10.54 | 1.19 | 11 | 59  | —   |
| 2 |    | 11.11 | —    | 12.12 | 13.61 | 12.28 | 1.26 | 10 | 68  | 17  |
| 7 |    | 6.75  | 9.77 | 12.92 | 10.85 | 10.07 | 2.58 | 26 | 56  | −4  |
| 9 |    | 8.23  | 10.5 | 10.57 | 11.02 | 10.08 | 1.25 | 12 | 56  | −4  | b

| Day | Nominal BiTE [µg/ml] | A 1 | A 2 | A 3 | A 4 | Average |
|-----|---------------------|-----|-----|-----|-----|---------|
| 0 | 0.05 | — | — | — | — | — |
| 2 |      | 91 | 98 | 111 | 109 | 102 |
| 7 |      | 84 | 96 | 101 | 92 | 93 |
| 9 |      | 75 | 85 | 83 | 72 | 79 |
| 0 | 0.7  | — | — | — | — | — |
| 2 |      | 71 | 106 | 136 | 136 | 112 |
| 7 |      | 86 | 87 | 82 | 108 | 91 |
| 9 |      | 113 | — | 88 | 84 | 95 |
| 0 | 2    | — | — | — | — | — |
| 2 |      | 68 | 83 | 113 | 112 | 94 |
| 7 |      | 58 | 89 | 75 | 104 | 82 |
| 9 |      | 135 | 104 | 90 | 95 | 106 |
| 0 | 18   | — | — | — | — | — |
| 2 |      | 105 | — | 115 | 129 | 117 |
| 7 |      | 64 | 93 | 123 | 103 | 96 |
| 9 |      | 78 | 100 | 100 | 105 | 96 |

Abbreviations used in tables 21a and b:
BiTE: PSMA-BiTE 1 molecule
A: Assay
Ave: Average
T0 value: Value at time 0

For use in the CytoTox-Glo Cytotoxicity Assay, it was necessary to dilute the assay solutions with assay medium, as follows:

18 µg/ml: 1:36

90 µg/ml 1:180

500 µg/ml 1:1000

2000 µg/ml 1:4000

The biological activity of the assay material is expressed as "relative bioactivity". It is determined as follows:

$$\text{Relative biological activity} = \frac{EC50 \text{ (reference standard)}}{EC50 \text{ (assay control)}}$$

Table 22 shows that the bioactivity of the final infusion solutions containing from 18 µg/ml to 2000 µg/ml PSMA-BiTE1 remains stable over a storage period of 9 days. The relative bioactivities vary during the storage time of 9 days, compared to the T0 value, within a range of 77%-132%. These results thus lie well within a previously determined acceptance range of 50% to 200% bioactivity.

TABLE 22 a

Determination of the relative potency by cell-based cytotoxicity assay within the range from 18 to 2000 µg/ml.

| Day | Nominal BiTE [µg/ml] | A 1 | A 2 | A 3 | A 4 | Ave | STDEV | CV [%] |
|-----|----------------------|-----|-----|-----|-----|-----|-------|--------|
| 0 | 18 | 0.87 | 1.08 | 0.75 | — | 0.9 | 0.17 | 19 |
| 2 |    | 1.1  | 0.88 | 0.85 | — | 0.94 | 0.14 | 15 |
| 7 |    | 0.82 | —    | —    | — | 0.82 | —    | —  |
| 9 |    | 0.56 | 0.83 | —    | — | 0.7  | 0.19 | 27 |
| 0 | 90 | 0.91 | 0.82 | 0.72 | — | 0.82 | 0.09 | 12 |
| 2 |    | 0.85 | 0.96 | 0.91 | — | 0.91 | 0.06 | 6  |
| 7 |    | 0.79 | —    | —    | — | 0.79 | —    | —  |
| 9 |    | 0.68 | 0.9  | —    | — | 0.79 | 0.16 | 20 |
| 0 | 500 | 0.81 | 0.92 | 0.93 | 0.89 | 0.89 | 0.05 | 6 |
| 2 |     | 1.35 | 1.18 | 0.99 | —    | 1.17 | 0.18 | 15 |
| 7 |     | 0.94 | 1.09 | —    | —    | 1.01 | 0.1  | 10 |
| 9 |     | 0.99 | 0.94 | —    | —    | 0.96 | 0.03 | 3  |
| 0 | 2000 | 0.87 | 1.12 | 0.64 | 0.71 | 0.84 | 0.21 | 25 |
| 2 |      | 0.79 | 1.24 | 1.25 | 0.84 | 1.03 | 0.25 | 24 |
| 7 |      | 0.74 | 0.91 | —    | —    | 0.83 | 0.12 | 15 |
| 9 |      | 0.97 | 0.94 | —    | —    | 0.96 | 0.02 | 2  |

TABLE 22-continued b
Determination of the relative bioactivity compared to the
T0 value by cell-based cytotoxicity assay within
the range from 18 to 2000 µg/ml.

| Day | Nominal BiTE [µg/ml] | Relative bioactivity compared to the T0 value [%] | | | | |
|---|---|---|---|---|---|---|
| | | A 1 | A 2 | A 3 | A 4 | Ave |
| 0 | 18 | — | — | — | — | — |
| 2 | | 123 | 97 | 94 | — | 105 |
| 7 | | 92 | — | — | — | 92 |
| 9 | | 63 | 92 | — | — | 77 |
| 0 | 90 | — | — | — | — | — |
| 2 | | 104 | 118 | 112 | — | 111 |
| 7 | | 97 | — | — | — | 97 |
| 9 | | 83 | 110 | — | — | 97 |
| 0 | 500 | — | — | — | — | — |
| 2 | | 152 | 133 | 112 | — | 132 |
| 7 | | 106 | 123 | — | — | 114 |
| 9 | | 111 | 107 | — | — | 109 |
| 0 | 2000 | — | — | — | — | — |
| 2 | | 95 | 148 | 149 | 100 | 123 |
| 7 | | 88 | 109 | — | — | 99 |
| 9 | | 116 | 113 | — | — | 115 |

Abbreviations used in table 22:
BiTE: PSMA-BiTE 1 molecule
A: Assay
Ave: Average
T0 value: Value at time 0

The differences in the bioactivity of solutions diluted and stored for 9 days were not greater than ±33% compared to the T0 values. There is no apparent trend indicating a distinct loss of bioactivity during the storage time. Assay solutions containing 18 µg/ml PSMA-BiTE1 exhibit a slight decrease in bioactivity during the storage time, but it was not possible to confirm this trend when the assay solutions of the higher concentrations are considered.

In addition, in the ECL assay, the concentration of 18 µg/ml exhibited no decrease in protein concentration over the storage time.

In summary, it can be stated that the storage of the final injection solutions of PSMA-BiTE1 within a concentration range of 18-2000 µg/ml, compatible with the dilution conditions used and with the storage and administration system, for up to 9 days at a temperature of +2-8° C., including a period of up to 20 hours at +20±5° C., is possible.

Example 22

Bioavailability of PSMA-BiTE1 Following Subcutaneous Administration

Using the formulation of 50 mM $Na_2HPO_4$, 100 mM TRIS, pH 6.0, 4% trehalose, 0.04% polysorbate 80, it is possible to achieve high bioavailability following subcutaneous administration. The s.c. bioavailability of the PSMA-BiTE1 molecules is examined in 4 female *Cynomolgus* monkeys. The dosage is 45 µg/kg for the s.c. administration and is compared to an i.v. administration of 5 and 15 µg/kg of body weight (BW). The 2 mg/ml stock solution is diluted with physiological saline solution. The infusion time of the i.v. administration is 1 hour and the infusion rate is 1 ml/kg BW. The selected site of injection is a superficial vein (*V. saphena parva*). For the s.c. administration, the test solution is injected into the lateral chest region at 0.15 ml/kg BW. The blood levels are examined using an ELISA assay. To this end, ECL technology is used. The lower limit of quantification (LLOQ) of the method is 4 µg/l.

Example 22a

Bioavailability of PSMA-BiTE1 Following Subcutaneous Administration

Using the formulation of 50 mM $Na_2HPO_4$, 100 mM TRIS, pH 6.0, 4% trehalose dihydrate, 0.04% polysorbate 80, it is possible to achieve 66% bioavailability following subcutaneous administration. The s.c. bioavailability of the PSMA-BiTE1 molecules was examined in 4 female *Cynomolgus* monkeys. The dosage was 45 µg/kg for the s.c. administration and was compared to an i.v. administration of 5 and 15 µg/kg of body weight (BW). The 2 mg/ml stock solution was diluted with physiological saline solution. The infusion time of the i.v. administration was 1 hour and the infusion rate was 1 ml/kg BW. The selected site of injection was a superficial vein (*V. saphena parva*). For the s.c. administration, the test solution was injected into the lateral chest region at 0.15 ml/kg BW. The blood levels were examined using an ELISA assay. To this end, ECL technology was used. The lower limit of quantification (LLOQ) of the method was 4 µg/l.

Methods

Production of the PSMA-BiTE Molecules

Methods for producing BiTE molecules, more particularly PSMA-BiTE molecules, are described in WO2010037836 A2 for example.

Firstly, the PSMA-BiTE1-encoding recombinant BiTE DNA construct was integrated into a suitable expression vector and stably introduced thereby into eukaryotic CHO (Chinese hamster ovary) cells. The transfected CHO cells were cultured in a bioreactor with a suitable culture medium and the secreted protein was isolated by filtration of the cells. The purification of the BiTE molecules comprised replacing the buffer substances with TRIS and phosphate by means of size-exclusion chromatography (SEC) and subsequent concentration by means of ultrafiltration and diafiltration. In addition, a polyol (preferably trehalose) and a wetting agent (preferably polysorbate 80) was added. The composition was stored at below −60° C.

Differential Scanning Fluorimetry (DSF)

The measurements on the stability of the PSMA-BiTE1 molecules (e.g. following shear stress) were carried out using a 7500 Fast Real-Time PCR System (Applied Biosystems). Different PSMA-BiTE1 concentrations (between 0.15 and 0.005 mg/ml) were admixed with a fluorescent dye (e.g. "Sypro® Orange 5000") in 96-well plates (microtitre plates) and measured in a PCR system (7500 Fast Real-Time PCR System, Applied Biosystems). The temperature was increased from 20° C. to 90° C. The melting points of the proteins were ascertained via fluorescence detection, which comes about in a temperature-dependent manner when the fluorescent dye reacts with the hydrophobic regions of the protein.

Differential Scanning Calorimetry (DSC)

The thermal unfolding temperature ($T_m$) of the PSMA-BiTE1 molecules was ascertained by means of DSC. For this purpose, the samples were heated from 20° C. to 105° C. and the melting point of the polypeptides was ascertained using a calorimeter. A VP-DSC instrument from GE Healthcare was used.

Agitation Stress

The samples were stressed by agitation on a laboratory shaker (IKA, HS 260) in a temperature-controlled chamber (MMM, FrioCell 200). The critical quality parameter of aggregation was ascertained after 24 hours at 300 rpm and 20° C.

Visual Check

The stability of PSMA-BITE solutions was visually checked after the shear stress by holding the solutions against a dark background and checking for visible particles or turbidity. A clear solution following the agitation stress test indicates little or no formation of dimers and/or multimers, whereas visible turbidity of the solution correlates with a high proportion of dimers and/or multimers.

Dynamic Light Scattering (DLS)

Dynamic light scattering is a method for analysing the scattered light of a laser on a dissolved or suspended sample. What is measured is the hydrodynamic radius, which in turn makes it possible to infer the aggregation state of the PSMA-BiTE1 molecules. The hydrodynamic radius was measured using a Horiba LB 550 (Retsch Technology).

Determination of the Protein Content

The protein content was measured spectrometrically at 280 nm using a Nanodrop 2000 (Thermo Scientific). All samples were measured against the corresponding placebo or buffer solutions.

Each sample solution was pipetted (2 μl) 3× into the measurement area of the Nanodrop instrument and measured in duplicate in each case; thereafter, these measured values (n=6) were averaged. The protein content [mg/ml] was calculated from the averaged measured values via a previously created protein calibration function (dependence of absorption in relation to protein content).

Electrochemiluminescent Measurement (ECL Assay)

For this method, use was made of SULFO-TAG™ labels, which emit light following electrochemical stimulation. Stimulation was carried out on the surfaces of electrodes of so-called MULTI-ARRAY microplates. The emitted light was measured at approx. 620 nm using a detector.

The measurement was based on the "sandwich" method, in which PSMA-BiTE1 molecules in solution have been immobilized on a microplate by means of polyclonal goat anti-PSMA-BiTE1 antibodies. Penta-His-biotin was then bound to the immobilized BiTE molecules and detected by means of SULFO-TAG™-conjugated streptavidin. The samples were read out in a Sector Imager 2400.

Size-Exclusion Chromatography (SEC)

To determine the proportions of monomers and dimers and also the low-molecular-weight (LMW) and high-molecular-weight (HMW) fractions, size-exclusion chromatography was carried out using an HPLC system. Measurement was carried out using a fluorescence detector and calculation was carried out by means of the area per cent method. The column used was a standard column for the SEC of proteins, for example a Tosoh Biosep TSK gel G3000 SWXL 5 μm, 300 mm length×7.8 mm i.D. or an equivalent material.

Determination of PSMA-BITE1 Concentrations in Serum Following i.v. and s.c. Administration The concentration of PSMA-BITE1 in the serum of *Cynomolgus* monkeys was measured by means of ELISA. Detection was carried out by means of electrochemiluminescence. The detection limit (LLOQ) was 0.98 μg/l, with a precision of from 3 to 28% and an accuracy of from 70 to 100%.

Cell-Based Activity Assay

The cell-based cytotoxicity assay is used as a routine assay for determining the relative activity of PSMA-BiTE1 samples. Owing to the bispecific binding of PSMA-BiTE1 to human/cynomolgus CD3-positive and human/cynomolgus PSMA-positive cells, T-cell-mediated lysis of the target cells takes places following activation of the T cells (effector cells).

Cytotoxicity is detected by means of the luminescent CytoTox-Glo Cytotoxicity Assay from Promega. The measured value used here is the amount of light signal released, which correlates with the number of dying cells. Further activity assays are described in WO2010037836 A2.

Cell-Based Cytotoxicity Assay for Determining the Relative Activity of the PSMA-BiTE1 Samples Instruments and Material
1. Laminar flow cabinet
2. Cell culture incubator
3. Microscope
4. Cell counter, for example haemocytometer
5. 96-well U-bottom plates, clear (e.g. Greiner Bio-one)
6. 96-well flat-bottom plates, white (e.g. Nunc, 3058078)
7. Cell culture flasks
8. Multi-plate measurement instrument Reagents
1. Effector cells, for example MC15
2. Target cells, for example C4-2
3. 0.4% Trypan blue
4. Penicillin-streptomycin
5. L-Glutamine (200 mM)
6. Interleukin 2
7. Medium—MC15: Advanced RPMI 1640
8. Foetal calf serum (FCS), for example Gibco 10270106
9. PBS, for example Gibco 20012
10. Medium—C4-2: RPMI 1640 with L-glutamine, for example Gibco 11835063
11. Detection reagent, for example CytoTox Glo, Promega G9291

Growth Media
Medium for MC15 cells, for example
900 ml of Advanced RPMI 1640
+100 ml of FCS
+10 ml of penicillin-streptomycin
+10 ml of L-glutamine (200 mM)
+10-20 μl of [100-200 U/ml] interleukin 2
Medium for C4-2 cells, for example
900 ml of RPMI 1640 with L-glutamine
+100 ml of FCS
+10 ml of penicillin-streptomycin Assay Medium
Assay medium, for example
900 ml of RPMI 1640 with L-glutamine
+100 ml of FCS Start of MC15 Cell Culture
Cells for the assay were kept in liquid nitrogen. The cells were thawed rapidly at 37° C. The cells were then re-suspended in 15 ml of cold medium and incubated for 10 min. The cells were then centrifuged for, for example, 7 minutes at 700 g, the supernatant discarded, and the pellet re-suspended in 10 ml of growth medium. Cells were incubated at 37° C. and 5% $CO_2$ for approx. 3-4 days.

Sub-Culturing of MC15
Aliquots of live cells from the culture are counted.
Centrifuge for 7 minutes at 170 g.
Discard the supernatant and adjust the pellet with growth medium to a concentration of $0.5\times10^6$ to $1.5\times10^6$ cells/ml. The cells should be passaged 2-3 times per week.

Start of C4-2 Cell Culture
Cells for the assay are kept in liquid nitrogen. The cells are thawed rapidly at 37° C. The cells are then re-suspended in 20 ml of medium. Then centrifuge for, for example, 7 minutes at 700 g. Discard the supernatant and re-suspend the pellet in 10 ml of growth medium.

Cells are incubated at 37° C. and 5% $CO_2$ for approx. 3-4 days.

Sub-Culturing of C4-2

Remove the medium from the flask and discard.
Carefully rinse the cell layer with 10 ml of PBS.
Add 2-3 ml of trypsin and incubate at 37° C. until the cell layer detaches (approx. 5-15 min)
Add 10 ml of medium and dissolve the cells.
Centrifuge for, for example, 7 minutes at 170 g.
Discard the supernatant and re-suspend the pellet in 10 ml of growth medium, count the cells, and adjust the cells with medium to a suitable density.
Cells are incubated at 37° C. and 5% $CO_2$ for approx. 3-5 days and should be passaged 1-2 times per week.

Preparation of the Cells for the Assay

Detach the cells as described above.
Adjust the effector cells (MC15) in assay medium to a concentration of 2×10E6 cells/ml.
Adjust the target cells (C4-2) in assay medium to a concentration of 4×10E5 cells/ml.
Mix equal volumes of target and effector cells 1:1 (cell mixture).

Preparation of the Samples, Assay Control and Reference Material

Equilibrate the sample(s), assay control and reference material (RF) to room temperature, mix well, and adjust them all with assay medium to the same first concentration (V1; for example 500 ng/ml). Then carry out a serial dilution (for example 1:6, n=7) using assay medium to obtain best-fit dose-response curves.

Test Procedure

Addition of the Samples, Assay Control and Reference Material

Transfer aliquots of samples, assay control and reference material (e.g. 25 µl) to the corresponding wells of a 96-well flat-bottom plate.
Transfer the cell mixture (e.g. 50 µl) to each well of a 96-well flat-bottom plate.
Agitate the plate for, for example, 1 min at 400 rpm.
Incubate the plate for 16-24 h at 37° C. and 5% $CO_2$.

Determining Cytotoxicity and Relative Activity

Addition of the Detection Reagent and Measurement

Dilution and addition of the reagent and also the subsequent measurement are carried out in accordance with the instructions from the manufacturer, for example CytoTox—Glo, Promega.
Add 15 µl of reagent per well.
Agitate the plate for, for example, 1 min at 400 rpm.
Incubate at room temperature for approx. 15 min.
The luminescence is measured using a suitable multi-plate measurement instrument.

Evaluation

Best-Fit Curve

Determine the mean measured values at each concentration for the replicates of the samples, assay control and reference material.
Draw a dose-response curve for each series of samples, assay control and reference material. For this purpose, the mean measured values are plotted against the final concentrations of BAY2010112 (e.g. 500 000 pg/ml to 1.79 pg/ml).
Fit a suitable best-fit curve through the mean measured values of the concentration levels of the samples, assay control and reference material.

Relative Activity (Determination)

The activity ratio between sample and reference material is determined and documented. Statistical software can be used.

Assessment

The relative activity of the sample compared to the reference material must correspond to the specification.

Determination of the Concentration of the PSMA-BiTE1 Polypeptides (UV/VIS Spectroscopy)

The method is carried out according to the European Pharmacopoeia (Ph. Eur., 2.2.25, UV-VIS spectroscopy at 280 nm) and is also suitable for determining the concentration of other molecules.

Firstly, the extinction coefficient of the PSMA-BiTE1 molecules was determined experimentally.

To this end, the absorbance of solutions of known PSMA-BiTE1 concentration was determined, the concentrations (in mol/l) being established on the basis of the molar mass of the PSMA-BiTE1 molecules ($1.8673 \times 10^5$ g/mol). On the basis of the absorbance, the path length and the concentration, it was possible to calculate the extinction coefficient e of PSMA-BiTE1 molecules, according to $$e = A/c \times d, \text{ where}$$

A=absorbance (or absorption, disregarding light scattering) at a suitable wavelength (in this case, 280 nm)
c=concentration (mol/l)
d=path length (mm)

The absorbance values were then plotted on the y-axis against the associated concentrations on the x-axis to obtain a standard curve. Using these standard curves, it was subsequently possible to directly read off the concentration of PSMA-BiTE1 solution on the basis of the absorbance.

To create the aforementioned standard curves, the Beer-Lambert law must be applicable to the solution measured, i.e., inter alia, the absorbing substance must be homogeneously distributed in the solution, the variation of the absorption coefficients within the spectral range measured must be negligible, and the solution measured must be concentrated to a sufficiently low level so that interaction-related deviations do not occur.

Using the extinction coefficient of a molecule, the protein concentration (in mol/l) can also be inversely calculated on the basis of the measured absorbance (or absorption at 280 nm), according to:

$$\text{Protein concentration [mol/l]} = A \times V/e \times d, \text{ where}$$

A=absorption at 280 nm
d=cell length in cm (standard cell, 1.00 cm)
V=dilution of the test solution
e=extinction coefficient of PSMA-BiTE1 at 280 nm=111 315 $M^{-1} \times cm^{-1}$.

The invention claimed is:

1. A liquid pharmaceutical composition comprising from 0.5 µg/ml to 3.0 mg/ml of a bispecific T-cell engager comprising the amino acid sequence of SEQ ID NO: 8, tris(hydroxymethyl)aminomethane in a concentration of 100 mM, and
phosphate in a concentration of 50 mM,
polysorbate 80 in a concentration of 0.04%, and
a lyoprotectant to prevent undesired degradation or aggregation of proteins during lyophilization,
wherein the pH of the composition is 5.0 to 7.5.

2. The composition according to Claim 1, wherein the lyoprotectant is present in an amount of 2-10% of the composition.

3. The composition according to Claim 1, wherein the lyoprotectant is trehalose or trehalose dihydrate.

4. The composition according to claim 1, further comprising about 4% trehalose dihydrate.

5. The composition according to claim 1, wherein the composition contains the bispecific T-cell engager in a concentration of about 2 mg/ml.

6. A lyophilized solids mixture of the liquid composition according to claim 1.

7. A liquid pharmaceutical composition, wherein the composition is reconstituted from the lyophilized solids mixture according to claim 6 in a suitable liquid medium.

8. The composition according to claim 1, wherein the bioavailability of the bispecific T-cell engager following subcutaneous administration of the composition is >60%.

9. A syringe comprising the composition according to claim 1.

* * * * *